United States Patent [19]

Yu et al.

[11] Patent Number: 4,518,789

[45] Date of Patent: May 21, 1985

[54] PHENYL ALPHA-ACYLOXYACETAMIDE DERIVATIVES AND THEIR THERAPEUTIC USE

[76] Inventors: Ruey J. Yu, 4 Lindenwold Ave., Ambler, Pa. 19002; Eugene J. Van Scott, 1138 Sewell Ln., Rydal, Pa. 19046

[21] Appl. No.: 495,159

[22] Filed: May 17, 1983

Related U.S. Application Data

[63] Continuation-in-part of Ser. No. 393,741, Jun. 30, 1982, abandoned.

[51] Int. Cl.$^3$ ............................................. C07C 69/76
[52] U.S. Cl. ...................... 560/105; 560/1; 560/106; 560/250; 560/252; 260/410.5; 564/170; 514/534; 514/544; 514/532; 514/546; 514/859; 514/861; 514/863
[58] Field of Search ................. 260/410.5; 560/1, 105, 560/106, 250, 252; 564/170; 424/309, 311, 320, 424/324

[56] References Cited

PUBLICATIONS

Koenig, W. A. et al., J. Chromolography 200, 189–194, 1980.

Primary Examiner—Paul J. Killos
Attorney, Agent, or Firm—LeBlanc, Nolan, Shur & Nies

[57] ABSTRACT

Therapeutic as well as preventive measures to alleviate the symptoms of dermatologic and other conditions and disorders with phenyl alpha-acyloxyacetamide derivatives is disclosed. Dermatologic and other conditions and disorders in humans in which the compounds may be useful include pruritus, atopic dermatitis, eczema, psoriasis, acne, dry skin, dandruff, malodors of integumental areas; and various aches, pains and discomforts of skin, joints and other body parts. The phenyl alpha-acyloxyacetamide derivatives include, for example, N-ethyl phenyl alpha-acetoxyacetamide, N-benzyl phenyl-alpha-acetoxyacetamide, N-phenethyl phenyl-alpha-acetoxyacetamide, N-benzyl diphenyl-alpha-acetoxyacetamide and N-phenethyl diphenyl-alpha-acetoxyacetamide. The compositions containing the active ingredients are also useful for treatment of skin conditions or disorders, and musculoskeletal disorders, of domestic animals, for example dogs, such as dry skin, scurf, eczema, mange, prurigo, malodors, arthritis or myositis. Some phenyl-alpha-acyloxyacetamide derivatives may have a tranquilizing effect.

21 Claims, No Drawings

PHENYL ALPHA-ACYLOXYACETAMIDE DERIVATIVES AND THEIR THERAPEUTIC USE

This is a continuation-in-part of our co-pending U.S. patent application Ser. No. 393,741, filed June 30, 1982, now abandoned, bearing the same title.

This invention relates generally to therapeutic treatment as well as preventive measures of dermatologic and other conditions and disorders by either topical or systemic administration of phenyl alpha-acyloxyacetamide derivatives. As will be subsequently described in detail, we initially discovered that alpha hydroxy or keto acids and their derivatives were effective in the topical treatment of disease conditions such as dry skin, ichthyosis, eczema, palmar and plantar hyperkeratoses, dandruff, acne and warts.

We have now discovered that phenyl alpha-acyloxyacetamide derivatives on topical or systemic administration are effective in therapeutic treatment as well as preventive measures of various dermatologic and other conditions and disorders in humans and animals.

In our prior U.S. patent application entitled "Treatment of Ichthyosiform Dermatoses", Ser. No. 394,269, filed Sept. 4, 1973, now U.S. Pat. No. 3,879,537, we described and claimed the use of certain alpha hydroxy acids, alpha keto acids and related compounds for topical treatment of fish-scale like Ichthyotic conditions in humans. In our U.S. patent application entitled "Treatment of Disturbed Keratinization", Ser. No. 445,231, filed Feb. 25, 1974, now U.S. Pat. No. 3,920,835, we described and claimed the use of these certain alpha hydroxy acids, alpha keto acids and their derivatives for topical treatment of dandruff, acne, and palmar and plantar hyperkeratosis.

In our prior U.S. patent application entitled "Treatment of Dry Skin", Ser. No. 720,835, filed Sept. 7, 1976, now U.S. Pat. No. 4,105,783, we described and claimed the use of alpha hydroxy acids, alpha keto acids and their derivatives for topical treatment of dry skin.

In our recent U.S. patent application entitled "Additives Enhancing Topical Corticosteroid Action", Ser. No. 65,332, filed Aug. 9, 1979, now U.S. Pat. No. 4,246,261, we described and claimed that alpha hydroxy acids, alpha keto acids and their derivatives, in small amounts could greatly enhance the therapeutic efficacy of corticosteroids in topical treatment of psoriasis, eczema, seborrheic dermatitis and other inflammatory skin conditions.

In our most recent U.S. patent application entitled "Alpha Hydroxyacids, Alpha Ketoacids and Their Use in Treating Skin Conditions", Ser. No. 145,240, filed Apr. 30, 1980, now U.S. Pat. No. 4,363,815, we described and claimed that alpha hydroxy acids and alpha keto acids related to or originating from amino acids, whether or not found in proteins, were effective in topical treatment of skin disorders associated with disturbed keratinization or inflammation. These skin disorders include dry skin, ichthyosis, palmar and plantar hyperkeratosis, dandruff, Darier's disease, lichen simplex chronicus, keratoses, acne, psoriasis, eczema, pruritus and possibly warts and herpes.

DESCRIPTION OF THE INVENTION

It has now been discovered that a class of new compounds named phenyl alpha-acyloxyacetamide derivatives can be therapeutically useful on topical or systemic administration against varieties of dermatologic and other conditions and disorders including pruritus, atopic dermatitis, eczema, psoriasis, acne, dry skin, dandruff, malodors of integumental areas and various discomforts and pains of diverse body parts in humans and animals.

In accordance with the present invention, phenyl alpha-acyloxyacetamide derivatives which are incorporated in therapeutic compositions for topical or systemic administration to prevent or alleviate the symptoms of dermatologic or other conditions and disorders are grouped in the following two categories.

The first category of phenyl alpha-acyloxyacetamide derivatives is N-alkyl or aralkyl phenyl alpha-acyloxyacetamides as shown by the following chemical structure:

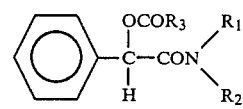

wherein
  $R_1$, $R_2$ = H, alkyl or aralkyl group of saturated or unsaturated, straight or branched chain or cyclic form, having 1 to 25 carbon atoms,
  $R_3$ = alkyl, aralkyl or aryl group of saturated or unsaturated, straight or branched chain or cyclic form, having 1 to 25 carbon atoms.

The hydrogen atom of the phenyl, $R_1$, $R_2$ or $R_3$ may be substituted by a nonfunctional element such as F, Cl, Br, I or a radical such as a lower alkyl or alkoxy of saturated or unsaturated, having 1 to 9 carbon atoms.

The carbon atom of $R_1$ or $R_2$ may be substituted by a nonfunctional N, S or O.

Phenyl alpha-acyloxyacetamide derivatives of this category may also exist as stereoisomers such as D, L and DL forms.

The typical alkyl or aralkyl group for $R_1$ or $R_2$ includes ethyl, isopropyl, t-butyl, allyl, cyclohexyl, benzyl, phenethyl, p-chlorobenzyl, p-methoxybenzyl, p-methoxyphenethyl, 3,4-dimethoxyphenethyl, diethylaminoethyl, hydroxyethylthioethyl, piperazinoethyl, p-fluorobenzyl, dimethylaminopropyl, diethylaminopropyl and picolyl. When one or more amino groups are present in $R_1$ or $R_2$, the compound may form a salt with inorganic or organic acid such as HCl or tartaric acid.

The typical alkyl, aralkyl or aryl group for $R_3$ includes methyl, ethyl, benzyl and phenyl.

The representative N-alkyl or aralkyl phenyl alpha-acyloxyacetamides which are useful for topical or systemic administration to alleviate dermatologic or other conditions or disorders are listed below:

1. N-ethyl phenyl-alpha-acetoxyacetamide $R_1 = C_2H_5$, $R_2 = H$, $R_3 = CH_3$ 2. N-phenethyl phenyl-alpha-acetoxyacetamide $R_1 = CH_2CH_2C_6H_5$, $R_2 = H$, $R_3 = CH_3$ 3. N-ethyl phenyl-alpha-phenylacetoxyacetamide $R_1 = C_2H_5$, $R_2 = H$, $R_3 = CH_2C_6H_5$ 4. N-phenethyl phenyl-alpha-phenylacetoxyacetamide $R_1=CH_2CH_2C_6H_5$, $R_2=H$, $R_3=CH_2C_6H_5$ 5. N-ethyl phenyl-alpha-benzoyloxyacetamide $R_1=C_2H_5$, $R_2=H$, $R_3=C_6H_5$ 6. N-benzyl phenyl-alpha-acetoxyacetamide $R_1=CH_2C_6H_5$, $R_2=H$, $R_3=CH_3$ 7. N-ethyl phenyl-alpha-propionyloxyacetamide $R_1=C_2H_5$, $R_2=H$, $R_3=C_2H_5$ 8. N-phenethyl phenyl-alpha-propionyloxyacetamide $R_1=CH_2CH_2C_6H_5$, $R_2=H$, $R_3=C_2H_5$ 9. N-allyl phenyl-alpha-acetoxyacetamide $R_1=C_3H_5$, $R_2=H$, $R_3=CH_3$ 10. N-ethyl phenyl-alpha-lauroyloxyacetamide $R_1=C_2H_5$, $R_2=H$, $R_3=C_{11}H_{23}$ 11. N-phenethyl phenyl-alpha-linoleoyloxyacetamide $R_1=CH_2CH_2C_6H_5$, $R_2=H$, $R_3=C_{17}H_{31}$ 12. N-phenethyl phenyl-alpha-linolenoyloxyacetamide $R_1=CH_2CH_2C_6H_5$, $R_2=H$, $R_3=C_{17}H_{29}$ 13. N,N-diethyl phenyl-alpha-acetoxyacetamide $R_1=C_2H_5$, $R_2=C_2H_5$, $R_3=CH_3$ 14. N-isopropyl phenyl-alpha-acetoxyacetamide $R_1=C_3H_7$, $R_2=H$, $R_3=CH_3$ 15. N-t-butyl phenyl-alpha-acetoxyacetamide $R_1=C_4H_9$, $R_2=H$, $R_3=CH_3$ 16. N-p-chlorobenzyl phenyl-alpha-acetoxyacetamide $R_1=CH_2C_6H_4Cl$, $R_2=H$, $R_3=CH_3$ 17. N-p-methoxybenzyl phenyl-alpha-acetoxyacetamide $R_1=CH_2C_6H_4OCH_3$, $R_2=H$, $R_3=CH_3$ 18. N-p-methoxyphenethyl phenyl-alpha-acetoxyacetamide $R_1=CH_2CH_2C_6H_4OCH_3$, $R_2=H$, $R_3=CH_3$ 19. N-(3,4-dimethoxyphenethyl)phenyl-alpha-acetoxyacetamide $R_1=CH_2CH_2C_6H_3(OCH_3)_2$, $R_2=H$, $R_3=CH_3$ 20. N-(N',N'-diethylaminoethyl)phenyl-alpha-acetoxyacetamide $R_1=CH_2CH_2N(C_2H_5)_2$, $R_2=H$, $R_3=CH_3$ 21. N-hydroxyethylthioethylphenyl-alpha-acetoxyacetamide $R_1=CH_2CH_2SCH_2CH_2OH$, $R_2=H$, $R_3=CH_3$ 22. N-piperazinoethyl phenyl-alpha-acetoxyacetamide $R_1=CH_2CH_2N(CH_2CH_2)_2NH$, $R_2=H$, $R_3=CH_3$ 23. N-(N',N'-diethylaminopropyl) phenyl-alpha-acetoxyacetamide $R_1=CH_2CH_2CH_2N(C_2H_5)_2$, $R_2=H$, $R_3=CH_3$ 24. N-(N',N'-dimethylaminopropyl) phenyl-alpha-acetoxyacetamide $R_1=CH_2CH_2CH_2N(CH_3)_2$, $R_2=H$, $R_3=CH_3$ 25. N-(2,3-dihydroxypropyl)phenyl-alpha-acetoxyacetamide $R_1=CH_2CHOHCH_2OH$, $R_2=H$, $R_3=CH_3$ 26. N,N-diethanol phenyl-alpha-acetoxyacetamide $R_1=CH_2CH_2OH$, $R_2=CH_2CH_2OH$, $R_3=CH_3$ 27. N-(2-phenylethanol)phenyl-alpha-acetoxyacetamide $R_1=CH_2CH(C_6H_5)OH$, $R_2=H$, $R_3=CH_3$ 28. N-(N',N'-diethanolaminopropyl)phenyl-alpha-acetoxyacetamide $R_1=CH_2CH_2CH_2N(CH_2CH_2OH)_2$, $R_2=H$, $R_3=CH_3$ 29. N-(1-ethyl-2,2'-dihydroxyisopropyl)phenyl-alpha-acetoxyacetamide $R_1=C(C_2H_5)(CH_2OH)_2$, $R_2=H$, $R_3=CH_3$ 30. N,N-dibenzyl phenyl-alpha-acetoxyacetamide $R_1=CH_2C_6H_5$, $R_2=CH_2C_6H_5$, $R_3=CH_3$ 31. N-hydroxyethoxyethyl phenyl-alpha-acetoxyacetamide $R_1=CH_2CH_2OCH_2CH_2OH$, $R_2=H$, $R_3=CH_3$ 32. N-diphenylmethyl phenyl-alpha-acetoxyacetamide $R_1=CH(C_6H_5)_2$, $R_2=H$, $R_3=CH_3$ 33. N-(2-phenyl-2'-hydroxyisopropyl)phenyl-alpha-acetoxyacetamide $R_1=CH(CH_2OH)CH_2C_6H_5$, $R_2=H$, $R_3=CH_3$ 34. N-(2-hydroxy-2-phenyl-2'-hydroxyisopropyl) phenyl-alpha-acetoxyacetamide $R_1=CH(CH_2OH)CH(OH)(C_6H_5)$, $R_2=H$, $R_3=CH_3$ 35. N-(2-hydroxyisopropyl)phenyl-alpha-acetoxyacetamide $R_1=CH(CH_2OH)CH_3$, $R_2=H$, $R_3=CH_3$ 36. N-(2-hydroxy-t-butyl)phenyl-alpha-acetoxyacetamide $R_1=C(CH_2OH)(CH_3)_2$, $R_2=H$, $R_3=CH_3$ 37. N-(1-methyl-2-ethylpyrrole)phenyl-alpha-acetoxyacetamide $R_1=CH_2CH_2C_4H_3NCH_3$, $R_2=H$, $R_3=CH_3$ 38. N-(1-methyl-2-ethylpyrrolidine)phenyl-alpha-acetoxyacetamide $R_1=CH_2CH_2C_4H_7NCH_3$, $R_2=H$, $R_3=CH_3$ 39. N-p-fluorobenzyl phenyl-alpha-acetoxyacetamide $R_1=CH_2C_6H_4F$, $R_2=H$, $R_3=CH_3$ 40. N-p-methylbenzyl phenyl-alpha-acetoxyacetamide $R_1=CH_2C_6H_4CH_3$, $R_2=H$, $R_3=CH_3$ 41. N-p-chlorophenethyl phenyl-alpha-acetoxyacetamide $R_1=CH_2CH_2C_6H_4Cl$, $R_2=H$, $R_3=CH_3$ 42. N-phenylpropyl phenyl-alpha-acetoxyacetamide $R_1=CH_2CH_2CH_2C_6H_5$, $R_2=H$, $R_3=CH_3$ 43. N-phenylbutyl phenyl-alpha-acetoxyacetamide $R_1=CH_2CH_2CH_2CH_2C_6H_5$, $R_2=H$, $R_3=CH_3$ During the syntheses of phenyl alpha-acyloxyacetamide derivatives of the instant invention certain intermediate products and related compounds which are not represented by the foregoing generic structures have also been tested for their therapeutic efficacy against dermatologic and other disorders and diseases. We have found that these intermediate products and related compounds are therapeutically effective but in general less so than phenyl alpha-acyloxyacetamide derivatives represented by the above generic structures. These intermediate products and related compounds are listed below:

1. N-ethyl phenyl-alpha-hydroxyacetamide
2. N-phenethyl phenyl-alpha-hydroxyacetamide
3. N-benzyl phenyl-alpha-hydroxyacetamide
4. N-isopropyl phenyl-alpha-hydroxyacetamide
5. N-t-butyl phenyl-alpha-hydroxyacetamide
6. N,N-diethyl phenyl-alpha-hydroxyacetamide
7. N-(N',N'-diethylaminoethyl)phenyl-alpha-hydroxyacetamide
8. N-piperazionethyl phenyl-alpha-hydroxyacetamide
9. N-allyl phenyl-alpha-hydroxyacetamide
10. N-P-chlorobenzyl phenyl-alpha-hydroxyacetamide
11. N-P-methoxybenzyl phenyl-alpha-hydroxyacetamide
12. N-P-methoxyphenethyl phenyl-alpha-hydroxyacetamide
13. N-(3,4-dimethoxyphenethyl)phenyl-alpha-hydroxyacetamide
14. N-hydroxyethylthioethyl phenyl-alpha-hydroxyacetamide
15. N-(N'N'-diethylaminopropyl)phenyl-alpha-hydroxyacetamide
16. N-P-fluorobenzyl phenyl-alpha-hydroxyacetamide
17. N-(N',N'-dimethylaminopropyl)phenyl-alpha-hydroxyacetamide The second category of phenyl alpha-acyloxyacetamide derivatives is N-alkyl or aralkyl phenyl alpha-alkyl aralkyl or aryl, alpha-acyloxyacetamides as shown by the following chemical structure:

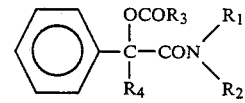

wherein $R_1$, $R_2=H$, alkyl or aralkyl group of saturated or unsaturated, straight or branched chain or cyclic form, having 1 to 25 carbon atoms, $R_3$ and $R_4=$alkyl, aralkyl or aryl group of saturated or unsaturated, straight or branched chain or cyclic form, having 1 to 25 carbon atoms.

The hydrogen atom of the phenyl, $R_1$, $R_2$, $R_3$ or $R_4$ may be substituted by a nonfunctional element such as F, Cl, Br, I or a radical such as a lower alkyl or alkoxy of saturated or unsaturated, having 1 to 9 carbon atoms.

The carbon atom of $R_1$ or $R_2$ may be substituted by a nonfunctional N, S or O.

Phenyl alpha-acyloxyacetamide derivatives of the second category may also exist as stereoisomers such as D, L and DL forms.

The typical alkyl or aralkyl group in $R_1$ or $R_2$ is ethyl, isopropyl, t-butyl, allyl, cyclohexyl, benzyl, phenethyl, p-chlorobenzyl, p-methoxybenzyl, p-methoxyphenethyl, 3,4-dimethoxyphenethyl, p-fluorobenzyl, diethylaminoethyl, hydroxyethylthioethyl, dimethylaminopropyl, piperazinoethyl, diethylamino propyl and picolyl. When one or more amino groups are present in $R_1$ or $R_2$ the compound may form a salt with inorganic or organic acid such as $H_2SO_4$ or citric acid.

The typical alkyl, arakyl or aryl group in $R_3$ or $R_4$ is methyl, ethyl, benzyl and phenyl.

The representative compounds of this second category of phenyl alpha-acyloxyacetamide derivatives are listed below:

1. N-ethyl diphenyl-alpha-acetoxyacetamide $R_1=C_2H_5$, $R_2=H$, $R_3=CH_3$, $R_4=C_6H_5$ 2. N-phenethyl diphenyl-alpha-acetoxyacetamide $R_1=CH_2CH_2C_6H_5$, $R_2=H$, $R_3=CH_3$, $R_4=C_6H_5$ 3. N-ethyl diphenyl-alpha-phenylacetoxyacetamide $R_1=C_2H_5$, $R_2=H$, $R_3=CH_2C_6H_5$, $R_4=C_6H_5$ 4. N-phenethyl diphenyl-alpha-phenylacetoxyacetamide $R_1=CH_2CH_2C_6H_5$, $R_2=H$, $R_3=CH_2C_6H_5$, $R_4=C_6H_5$ 5. N-ethyl phenyl alpha-methyl-alpha-acetoxyacetamide $R_1=C_2H_5$, $R_2=H$, $R_3=CH_3$, $R_4=CH_3$ 6. N-phenethyl phenyl alpha-methyl-alpha-acetoxyacetamide $R_1=CH_2CH_2C_6H_5$, $R_2=H$, $R_3=CH_3$, $R_4=CH_3$ 7. N-isopropyl diphenyl alpha-acetoxyacetamide $R_1=C_3H_7$, $R_2=H$, $R_3=CH_3$, $R_4=C_6H_5$ 8. N-t-butyl diphenyl alpha-acetoxyacetamide $R_1=C_4H_9$, $R_2=H$, $R_3=CH_3$, $R_4=C_6H_5$ 9. N-benzyl diphenyl-alpha-acetoxyacetamide $R_1=CH_2C_6H_5$, $R_2=H$, $R_3=CH_3$, $R_4=C_6H_5$ 10. N-allyl diphenyl-alpha-acetoxyacetamide $R_1=C_3H_5$, $R_2=H$, $R_3=CH_3$, $R_4=C_6H_5$ 11. N-phenethyl diphenyl-alpha-propionyloxyacetamide $R_1=CH_2CH_2C_6H_5$, $R_2=H$, $R_3=C_2H_5$, $R_4=C_6H_5$ 12. N-ethyl diphenyl-alpha-linolenoyloxyacetamide $R_1=C_2H_5$, $R_2=H$, $R_3=C_{17}H_{29}$, $R_4=C_6H_5$ 13. N-ethyl-N-methyl diphenyl-alpha-acetoxyacetamide $R_1=C_2H_5$, $R_2=CH_3$, $R_3=CH_3$, $R_4=C_6H_5$ 14. N,N-diethyl diphenyl-alpha-acetoxyacetamide $R_1=C_2H_5$, $R_2=C_2H_5$, $R_3=CH_3$, $R_4=C_6H_5$ 15. N-P-chlorobenzyl diphenyl-alpha-acetoxyacetamide $R_1=CH_2C_6H_4Cl$, $R_2=H$, $R_3=CH_3$, $R_4=C_6H_5$ 16. N-P-methoxybenzyl diphenyl-alpha-acetoxyacetamide $R_1=CH_2C_6H_4OCH_3$, $R_2=H$, $R_3=CH_3$, $R_4=C_6H_5$ 17. N-P-methoxyphenethyl diphenyl-alpha-acetoxyacetamide $R_1=CH_2CH_2C_6H_4OCH_3$, $R_2=H$, $R_3=CH_3$, $R_4=C_6H_5$ 18. N-(3,4-dimethoxy phenethyl)diphenyl-alpha-acetoxyacetamide $R_1=CH_2CH_2C_6H_3(OCH_3)_2$, $R_2=H$, $R_3=CH_3$, $R_4=C_6H_5$ 19. N-(N',N'-diethylaminoethyl) diphenyl-alpha-acetoxyacetamide $R_1=CH_2CH_2N(C_2H_5)_2$, $R_2=H$, $R_3=CH_3$, $R_4=C_6H_5$ 20. N-hydroxyethylthioethyl diphenyl-alpha-acetoxyacetamide $R_1=CH_2CH_2SCH_2CH_2OH$, $R_2=H$, $R_3=CH_3$, $R_4=C_6H_5$ 21. N-(N',N'-diethylaminopropyl) diphenyl-alpha-acetoxyacetamide $R_1=CH_2CH_2CH_2N(C_2H_5)_2$, $R_2=H$, $R_3=CH_3$, $R_4=C_6H_5$ 22. N-(N',N'-dimethylaminopropyl) diphenyl-alpha-acetoxyacetamide $R_1=CH_2CH_2CH_2N(CH_3)_2$, $R_2=H$, $R_3=CH_3$, $R_4=C_6H_5$ 23. N-piperazinoethyl diphenyl-alpha-acetoxyacetamide $R_1=CH_2CH_2N(CH_2CH_2)_2NH$, $R_2=H$, $R_3=CH_3$, $R_4=C_6H_5$ 24. N-(2,3-dihydroxypropyl) diphenyl-alpha-acetoxyacetamide $R_1=CH_2CHOHCH_2OH$, $R_2=H$, $R_3=CH_3$, $R_4=C_6H_5$ 25. N,N-diethanol diphenyl-alpha-acetoxyacetamide $R_1=CH_2CH_2OH$, $R_2=CH_2CH_2OH$, $R_3=CH_3$, $R_4=C_6H_5$ 26. N-(2-phenylethanol) diphenyl-alpha-acetoxy-acetamide $R_1=CH_2CH(C_6H_5)OH$, $R_2=H$, $R_3=CH_3$, $R_4=C_6H_5$ 27. N-(N',N'-diethanolaminopropyl) diphenyl-alpha-acetoxyacetamide $R_1=CH_2CH_2CH_2N(CH_2CH_2OH)_2$, $R_2=H$, $R_3=CH_3$, $R_4=C_6H_5$ 28. N-(1-ethyl-2,2'-dihydroxyisopropyl) diphenyl-alpha-acetoxyacetamide $R_1=C(C_2H_5)(CH_2OH)_2$, $R_2=H$, $R_3=CH_3$, $R_4=C_6H_5$ 29. N-p-fluorobenzyl diphenyl-alpha-acetoxyacetamide $R_1=CH_2C_6H_4F$, $R_2=H$, $R_3=CH_3$, $R_4=C_6H_5$ 30. N-p-methylbenzyl dephenyl-alpha-acetoxyacetamide $R_1=CH_2C_6H_4CH_3$, $R_2=H$, $R_3=CH_3$, $R_4=C_6H_5$ 31. N-p-cholorophenethyl dephenyl-alpha-acetoxyacetamide $R_1=CH_2CH_2C_6H_4Cl$, $R_2=H$, $R_3=CH_3$, $R_4=C_6H_5$ 32. N-phenylpropyl diphenyl-alpha-acetoxyacetamide $R_1=CH_2CH_2CH_2C_6H_5$, $R_2=H$, $R_3=CH_3$, $R_4=C_6H_5$ 33. N-phenylbutyl diphenyl-alpha-acetoxyacetamide $R_1=CH_2CH_2CH_2CH_2C_6H_5$, $R_2=H$, $R_3=CH_3$, $R_4=C_6H_5$ As with the first category of derivatives, certain intermediate products and related compounds of N-alkyl or aralkyl phenyl alpha-alkyl, aralkyl or aryl, alpha-acyloxyacetamides which are not represented by the generic structures have also been tested for their therapeutic efficacy against dermatologic and other disorders and diseases. We have found that these intermediate products and related compounds are therapeutically efficacious to a degree but less than the acylated derivatives represented by the foregoing generic structures. These intermediate products and related compounds are listed below:

1. N-ethyl diphenyl-alpha-hydroxyacetamide
2. N-phenethyl diphenyl-alpha-hydroxyacetamide
3. N-benzyl diphenyl-alpha-hydroxyacetamide
4. N,N-diethyl diphenyl-alpha-hydroxyacetamide
5. N-(N',N'-diethylaminoethyl)diphenyl-alpha-hydroxyacetamide
6. N-(N',N'-diethylaminopropyl) diphenyl-alpha-hydroxyacetamide
7. N-(N',N'-dimethylaminopropyl) diphenyl-alpha-hydroxyacetamide
8. N-p-methoxybenzyl diphenyl-alpha-hydroxyacetamide
9. N-p-chlorobenzyl diphenyl-alpha-hydroxyacetamide
10. N-p-methoxyphenethyl diphenyl-alpha-hydroxyacetamide
11. N-3,4-dimethoxyphenethyl diphenyl-alpha-hydroxyacetamide
12. N-hydroxyethylthioethyl diphenyl-alpha-hydroxyacetamide
13. N-isopropyl diphenyl-alpha-hydroxyacetamide
14. N-t-butyl diphenyl-alpha-hydroxyacetamide
15. N-allyl diphenyl-alpha-hydroxyacetamide Other heterocyclic ring derivatives of phenyl alpha-acyloxyacetamide have been synthetized and tested for their therapeutic efficacy against dermatologic and other disorders and diseases. We have found that other phenyl alpha-acyloxyacetamide derivatives with heterocyclic ring substitution are therapeutically effective but with various ranges of efficacy. These compounds are listed below:

1. N-3'-picolyl   phenyl-alpha-hydroxyacetamide
2. N-3'-picolyl   diphenyl-alpha-hydroxyacetamide
3. N-3'-picolyl   phenyl-alpha-acetoxyacetamide
4. N-3'-picolyl   diphenyl-alpha-acetoxyacetamide
5. N-3'picolyl    phenyl-alpha-phenylacetoxy-acetamide
6. N-3'picolyl    diphenyl-alpha-phenylacetoxy-acetamide Phenyl alpha-acyloxyacetamide derivatives of the instant invention may also be utilized in combination with or in small amounts as additives to enhance therapeutic effects of other drugs such as corticosteroids of either synthetic or nonsynthetic origin to alleviate the symptoms of prurigo, atopic dermatitis, psoriasis, acne, eczema, seborrheic dermatitis and other skin conditions characterized by inflammation, disturbed keratinization and pruritus. Commonly used corticosteroids include hydrocortisone, hydrocortisone-21-acetate, hydrocortisone-17-valerate, hydrocortisone-17-butyrate, triamcinolone acetonide, betamethasone and prednisone.

Phenyl-alpha-acyloxyacetamide derivatives may also be utilized in combination with other dermatologic drugs for topical, intravaginal or systemic administration to alleviate the symptoms of dermatitis and/or pruritus caused by fungal, bacterial or viral infection or by parasitic infestations. Commonly used topical, intravaginal or oral agents for the above infections and infestations include antiyeast, anti-fungal, antibacterial, antiviral, anti-inflammatory, keratolytic, antipsoriatic and antieczematic agents such as clotrimazole, miconazole, nystatin, neomycin, gramicidin, haloprogin, griseofulvin, salicylic acid, sodium thiosulfate, selenium sulfide, zinc pyrithione, benzyl benzoate, crotamiton, lindane, phenol, menthol, amphoterioins, penicillins, corticosteroids, antihistamines, antibiotics, anthralin, tar preparations and the like.

It has already been established through tests in animals and humans that phenyl alpha-acyloxyacetamide derivatives are therapeutically effective for topical or systemic treatment of various dermatologic and other conditions. For example, in topical treatment of pruritus ani N-ethyl phenyl-alpha-acetoxyacetamide and N-phenethyl phenyl-alpha-acetoxyacetamide in a concentration of from 1 to 5 percent are therapeutically effective when topically applied on a regular basis to cause complete relief from itching and scratching. In systemic treatment of domestic dogs for common scratching N-ethyl phenyl-alpha-acetoxyacetamide or N-phenethyl phenyl-alpha-acetoxyacetamide given orally in a single dose of 5 to 10 mg per kg body weight has been found to be therapeutically effective in relieving scratching for more than 8 hours.

Accordingly, it is an object of this invention to provide medicinal compositions containing at least one phenyl alpha-acyloxyacetamide derivative which when topically or systemically administered will substantially alleviate the symptoms of various dermatologic and other conditions and disorders.

It is another object of this invention to provide methods for treating various dermatologic and other conditions with topical preparations or systemic compositions containing phenyl-alpha-acyloxyacetamide derivatives.

PREPARATION OF THE THERAPEUTIC COMPOSITIONS

Phenyl alpha-acyloxyacetamide derivatives of the instant invention may be formulated either for topical application or for systemic administration. In the topical preparations phenyl alpha-acyloxyacetamide derivatives may be formulated in solution, lotion, gel, shampoo, spray, stick, powder, cream or ointment containing from 0.01 to 50 percent and preferably from about 0.1 to 10 percent by weight of the total composition.

To prepare a typical solution form phenyl alpha-acyloxyacetamide derivatives are initially dissolved in ethanol or acetone. Propylene glycol, water, glycerol, butanediol or the like may be added to the compositions. For example a typical therapeutic solution containing 5% N-ethyl phenyl-alpha-acetoxyacetamide is formulated in ethanol, water and propylene glycol in a volume ratio of 50:30:20, respectively.

Phenyl alpha-acyloxyacetamide derivatives in a lotion, cream or ointment composition may be formulated as follows. Phenyl alpha-acyloxyacetamide derivatives are intially dissolved in ethanol, acetone, or propylene glycol. The solution thus prepared may be admixed in a conventional manner with commonly available lotion, cream or ointment bases such as hydrophilic ointment U.S.P.

A typical gel composition of this invention utilizes at least one of the phenyl alpha-acyloxyacetamide derivatives, dissolved in a mixture of ethanol, water and propylene glycol in a volume ratio of 40:40:20, respectively. A gelling agent such as hydroxyethylcellulose, hydroxypropylcellulose or hydroxypropylmethylcellulose is then added to the mixture with agitation. The preferred concentration of the gelling agent may range from 0.1 to 3 percent by weight of the total composition.

To prepare a typical shampoo formulation phenyl alpha-acyloxyacetamide derivatives are disolved in a mixture of ethanol, water and propylene glycol. A surfactant such as triethanolaminelaurylsulfate may then be added to the solution.

For systemic use the phenyl alpha-acyloxyacetamide derivatives may be formulated for oral administration or for parenteral injections. In oral preparations the phenyl alpha-acyloxyacetamide derivatives may be formulated in tablet form or in gelatin capsules with or without mixing with gelatin powder. Each tablet or capsule may contain from 10 to 300 mg of a phenyl alpha-acyloxyacetamide derivative. For parenteral injections the phenyl alpha-acyloxyacetamide derivatives are prepared under sterilized conditions usually in 1 to 10 percent concentration in water or saline as solubilized form or fine suspension.

The following are illustrative examples of syntheses, formulations and compositions according to this invention. Although the examples utilize only selected formulations useful accordingly to this invention, it should be understood that the following examples are illustrative and not limited. Therefore, any of the aforementioned phenyl alpha-acyloxyacetamide derivatives may be substituted according to the teachings of this invention in the following examples:

EXAMPLE 1

Synthesis of N-ethyl phenyl alpha-acetoxyacetamide

The following method may be applied to synthesis of all N-alkyl phenyl alpha-acetoxyacetamides.

Mandelic acid ethyl ester 400 ml and ethylamine 70% in water, 400 ml are heated to 60 degrees C. for 5 hours. The mixture is then evaporated at 50 degrees C. in vacuum to remove water, excess ethylamine and other volatile components. The residue on standing at room temperature forms crystalline N-ethyl mandelic amide 350 g.

N-ethyl mandelic amide 50 g synthesized as above is dissolved in acetic anhydride 200 ml, and concentrated sulfuric acid 1 ml is added. The mixture is heated at 80–90 degrees C. for 5 hours to complete the acetylation. After evaporating at 60 degrees C. in vacuum a syrupy residue thus obtained is mixed with 400 ml of ice water. The oily product is extracted with chloroform 300 ml, and is washed with 5% aqueous sodium bicarbonate 200 ml and 0.5N HCL 200 ml, and is dried with anhydrous sodium sulfate. On evaporation of the chloroform solution at 40 degrees C. in vacuum white crystalline product is formed from the syrupy residue, and the crystals are washed with ether. N-ethyl phenyl alpha-acetoxyacetamide 32 g thus synthesized is identified by infrared spectroscopy, high performance liquid chromotography and thin-layer chromatography with a mobility of 0.79 on a solvent system of benzene:methanol 1:1.

EXAMPLE 2

N-ethyl phenyl alpha-acetoxyacetamide 5% solution may be formulated as follows.

N-ethyl phenyl alpha-acetoxyacetamide 5 g is dissolved in 95 ml solution prepared from ethanol, water and propylene glycol in a volume ratio of 50:30:20, respectively. The therapeutic solution thus prepared is suitable for topical administration, for example on hairy skin of domestic dogs and on scalp of humans.

EXAMPLE 3

N-ethyl phenyl alpha-acetoxyacetamide 5% cream may be formulated as follows.

N-ethyl phenyl alpha-acetoxyacetamide 5 g is dissolved in ethanol 15 ml, and the solution is mixed with 80 g of hydrophilic ointment USP. Continue mixing until a uniform consistency is obtained.

EXAMPLE 4

N-ethyl phenyl alpha-acetoxyacetamide 7% gel may be formulated as follows.

N-ethyl phenyl alpha-acetoxyacetamide 7 g is dissolved in 50 ml of ethanol, 20 ml of propylene glycol and 21 ml of water. Hydroxypropylcellulose 2 g is added to the mixture with agitation. Continue agitation until a uniform gel is formed.

EXAMPLE 5

N-ethyl phenyl alpha-acetoxyacetamide 3% composition in water-nonwashable cream may be formulated as follows:

| Part A: | Sorbitan sesquioleate | 10 g |
|---|---|---|
|  | Petrolatum | 15 g |
|  | Mineral oil | 15 g |
|  | Beeswax | 15 g |
|  | Isopropyl myristate | 10 g |
| Part B: | Water | 20 ml |
|  | Propylene glycol | 5 ml |
|  | Glycerol | 5 ml |
|  | Sorbitol | 5 g |
|  | Magnesium oxide | 0.1 g |

Heat Part A and Part B to 80 degrees C. Add Part B slowly to Part A with agitation. Continue agitation until the mixture is congealed. Add 10% aqueous phosphoric acid 0.5 ml and aluminum chlorohydroxide 0.5 g followed by 3 g of powdered N-ethyl phenyl alpha-acetoxyacetamide.

EXAMPLE 6

Synthesis of N-phenethyl phenyl alpha-acetoxyacetamide

The following method may be applied to synthesis of all N-aralkyl phenyl alpha-acetoxyacetamides.

Mandelic acid ethyl ester 190 ml and phenethylamine 190 ml are heated to 70–80 degrees C. for 2 hours. The mixture is then mixed with 2 liters of cold water, and white crystals thus formed are washed with 1 liter of 5% sodium carbonate solution. N-phenethyl mandelic amide 272 g thus prepared is suitable for the following synthesis of N-phenethyl phenyl alpha-acetoxyacetamide.

N-phenethyl mandelic amide 100 g synthesized as above is dissolved in acetic anhydride 230 ml, and concentrated sulfuric acid 0.5 ml is added. The mixture is heated at 70–80 degrees C. for 3 hours to complete the acetylation. After evaporation at 70–80 degrees C. in vacuum a syrupy residue thus obtained is mixed with 1.5 liters of cold water. Sodium bicarbonate powder 100 g is added to the mixture and the product is extracted with 300 ml of chloroform, and is dried with anhydrous sodium sulfate. On evaporation of chloroform white crystals are formed from a syrupy residue. The crystals are thoroughly washed with n-hexane, yield is 72 g. N-phenethyl phenyl alpha-acetoxyacetamide thus synthesized is identified by infrared spectroscopy, high performance liquid chromatography and thin-layer chromatography with a mobility of 0.66 on a solvent system of benzene:methanol 1:1.

EXAMPLE 7

N-phenethyl phenyl alpha-acetoxyacetamide 3% solution may be formulated as follows.

N-phenethyl phenyl alpha-acetoxyacetamide 3 g is dissolved in 97 ml solution prepared from ethanol, water and 1,3-butanediol in a volume ratio of 60:20:20, respectively. The therapeutic solution thus prepared may be stored in amber glass dropper bottles.

EXAMPLE 8

N-phenethyl phenyl alpha-acetoxyacetamide 4% cream may be formulated as follows.

N-phenethyl phenyl alpha-acetoxyacetamide 4 g is dissolved in 12 ml of ethanol, and the solution is mixed with 84 g of hydrophilic ointment USP. Continue mixing until a uniform consistency is obtained.

EXAMPLE 9

Synthesis of N-methyl phenyl alpha-acetoxyacetamide

Mandelic acid ethyl ester 250 ml and methylamine 40% in water, 400 ml are heated to 60–70 degrees C. for 3 hours. The mixture is evaporated at 50 degrees C. in vacuum to remove water, excess methylamine and other volatile materials. The residue on standing at room temperature forms crystalline N-methyl mandelic amide 207 g.

N-methyl mandelic amide 100 g, synthesized as above is dissolved in acetic anhydride 200 ml at 60 degrees C. and concentrated sulfuric acid 0.5 ml is added. The mixture is heated at 90–95 degrees C. for 5 hours to complete the acetylation. The reaction mixture is then evaporated at 70 degrees C. in vacuum and the syrupy residue thus obtained is mixed with 1 liter of ice water. Chloroform 200 ml is added to extract the oily product and the chloroform layer is washed with 5% aqueous sodium bicarbonate, 200 ml and 0.2N HCL 200 ml, and dried with anhydrous sodium sulfate. On evaporation of the chloroform solution at 40 degrees C. in vacuum white crystalline product is formed from the syrupy residue. The crystals are washed with n-hexane. N-methyl phenyl alpha-acetoxyacetamide 66 g thus synthesized is identified by infrared spectroscopy, high performance liquid chromatography and thin-layer chromatography with a mobility of 0.65 on a solvent system of benzene:methanol 1:1.

EXAMPLE 10

Synthesis of N-ethyl phenyl-alpha-lauroyloxyacetamide

The following method may be applied to synthesis of all N-alkyl phenyl-alpha-lauroyloxyacetamides.

N-ethylmandelic amide 17.9 g is dissolved in 50 ml of pyridine, and lauroyl chloride 22 ml is added with stirring. Exothermic acylation takes place immediately, and the reaction mixture becomes a semi-solid. After 16 hours at room temperature the mixture is mixed with 800 ml of cold 0.5N HCL solution. White crystals thus formed are isolated by filtration, washed with 1% sodium bicarbonate solution, water and dried at 50 degrees C. in a vacuum.

N-ethyl phenyl-alpha-lauroyloxyacetamide 27 g thus synthesized is identified by infrared spectroscopy, high performance liquid chromatography and thin-layer chromatography with a mobility of 0.83 on a solvent system of benzene:methanol 1:1.

EXAMPLE 11

Synthesis of N-ethyl phenyl-alpha-phenylacetoxyacetamide

The following method may be applied to synthesis of all N-ethyl phenyl-alpha-acyloxyacetamides.

N-ethyl mandelic amide 90 g is dissolved in 200 ml of pyridine, and phenylacetyl chloride 100 ml is added with stirring. The reaction mixture is cooled externally with ice water bath. The acylation takes place immediately with a formation of precipitates. The stirring is continued for 3 hours and the reaction mixture is mixed with 800 ml of cold water. The product is extracted with 300 ml of chloroform, and the chloroform layer is washed with 300 ml of sodium bicarbonate solution, followed by 300 ml of 0.5N HCL and is dried over anhydrous sodium sulfate. On evaporation of chloroform a syrupy product 145 g is obtained.

N-ethyl phenyl-alpha-phenylacetoxyacetamide thus synthesized is identified by infrared spectroscopy, high performance liquid chromatography and thin-layer chromatography with a mobility of 0.87 on a solvent system of benzene:methanol 1:1.

EXAMPLE 12

Synthesis of N-benzyl phenyl-alpha-acetoxyacetamide

Mandelic acid methyl ester 250 g and benzylamine 250 ml are heated at 60–70 degress C. for 3 hours. After standing at room temperature for 16 hours the reaction mixture forms white crystalline products. The crystals are washed with water and are dried at 40 degrees C. in vacuum. N-benzyl mandelic amide 375 g thus prepared is suitable for the following synthesis of N-benzyl phenyl-alpha-acetoxyacetamide.

N-benzyl mandelic amide 100 g is suspended in 250 ml of acetic anhydride and the mixture is heated to 60 degrees C. After all the solid materials have been dissolved in acetic anhydride concentrated sulfuric acid 0.5 ml is added to the solution. Acetylation takes place instantly with exothermic reaction and the reaction mixture turns reddish in color. After the initial exothermic reaction has subsided the mixture is heated to 90–100 degrees C. for 5 hours to complete the acetylation. The reaction mixture is then evaporated at 70–80 degrees C. in vacuum to remove acetic acid, water and the like. The residue is mixed with 300 ml of chloroform. The chloroform layer is washed with 300 ml of 5% aqueous sodium bicarbonate solution, water and dried over anhydrous sodium sulfate. On evaporation of chloroform solution crystalline product 113 g is obtained.

N-benzyl phenyl-alpha-acetoxyacetamide thus synthesized is identified by infrared spectroscopy, high performance liquid chromatography and thin-layer chromatography with a mobility of 0.56 on a solvent system of benzene:methanol 1:1.

EXAMPLE 13

Synthesis of N-phenethyl phenyl-alpha-benzoxyacetamide

N-phenethyl mandelic amide 51 g is dissolved in 200 ml of pyridine, and benzoyl chloride 42 ml is added with stirring. Exothermic benzoylation takes place immediately and the reaction mixture is cooled externally with a cold water bath. The stirring is continued for 5 hours, and the reaction mixture is mixed with 1 liter of ice water. The product is extracted with 250 ml of chloroform, washed with 300 ml of 5% sodium bicarbonate, followed by 300 ml of 0.5N HCL and is dried over anhydrous sodium sulfate. On evaporation of chloroform a crystalline product is obtained. The crystals are washed with n-hexane and dried. The yield is 85 g.

N-phenethyl phenyl-alpha-benzoxyacetamide thus synthesized is identified by infrared spectroscopy, high performance liquid chromatography and thin-layer chromatography with a mobility of 0.81 on a solvent system of benzene:methanol 1:1.

EXAMPLE 14

Synthesis of N-(N',N'-diethylaminoethyl)phenyl-alpha-acetoxyacetamide

Mandelic acid methyl ester 166 g and N,N-diethylaminoethylamine 200 ml are heated at 60-70 degrees C. for 3 hours. After standing at room temperature for 16 hours the reaction mixture forms white crystalline products. The crystals are washed with n-hexane and dried at 40 degrees C. in vacuum. N-(N',N'-diethylaminoethyl) mandelic amide 196 g thus prepared is suitable for the following synthesis.

N-(N',N'-diethylaminoethyl) mandelic amide 80 g is dissolved in 200 ml of acetic anhydride and the mixture is heated to 60 degrees C. Concentrated sulfuric acid 0.5 ml is added to the solution and the acetylation takes place immediately with slight exothermic reaction. The reaction mixture is heated to 100-105 degrees C. for 8 hours to complete the acetylation. The mixture is then evaporated at 70-80 degrees C. in vacuum to remove acetic acid, water and the like. The residue is mixed with 500 ml of 5% sodium bicarbonate and the product is extracted with 200 ml of chloroform. The chloroform layer is washed with 300 ml of 5% sodium bicarbonate solution and is dried over anhydrous sodium sulfate. On evaporation of chloroform solution a syrupy product 62 g is obtained.

N-(N',N'-diethylaminoethyl) phenyl-alpha-acetoxyacetamide thus synthesized is identified by infrared spectroscopy, high performance liquid chromatography and thin-layer chromatography with a mobility of 0.46 on a solvent system of benzene:methanol 1:1.

EXAMPLE 15

Synthesis of N-phenethyl phenyl-alpha-(o-acetylmandeloyloxy)acetamide

N-phenethyl mandelic amide 51 g is dissolved in 150 ml of pyridine, and o-acetylmandelic acid chloride 60 ml is added with stirring. Exothermic acylation takes place immediately and the stirring is continued for 5 hours. The reaction mixture is mixed with 1 liter of cold 0.2N HCL. The sticky solid thus formed is extracted with 300 ml of chloroform, washed with 400 ml of 5% sodium bicarbonate and is dried over anhydrous sodium sulfate. On evaporation of chloroform a syrupy product 98 g is obtained.

N-phenethyl phenyl-alpha-(o-acetylmandeloyloxy)acetamide thus synthesized is identified by infrared spectroscopy, high performance liquid chromatography and thin-layer chromatography with a mobility of 0.62 on a solvent system of benzene:methanol 1:1.

EXAMPLE 16

Synthesis of N-phenethyl phenyl-alpha-linoleoyloxyacetamide

The following method may be applied to synthesis of all N-aralkylphenyl-alpha-linoleoyloxyacetamides.

N-phenethyl mandelic amide 25.5 g is dissolved in 50 ml of pyridine, and linoleoyl chloride 30 ml is added with stirring. Exothermic acylation takes place immediately and the stirring is continued for 5 hours. The reaction mixture is mixed with 800 ml of 0.5N HCL and the product is extracted with 200 ml of chloroform. The chloroform solution is washed with 200 ml of 0.5N HCL, 200 ml of 5% sodium bicarbonate, 200 ml of water then is dried over anhydrous sodium sulfate. On evaporation of chloroform a syrupy product 42 g is obtained.

N-phenethyl phenyl-alpha-linoleoyloxyacetamide thus synthesized is identified by infrared spectroscopy, high performance liquid chromatography and thin-layer chromatography with a mobility of 0.80 on a solvent system of benzene:methanol 1:1.

EXAMPLE 17

Synthesis of N,N-diethyl phenyl-alpha-acetoxyacetamide

The following method may be applied to synthesis of all N,N-dialkyl phenyl-alpha-acetoxyacetamides.

Mandelic acid ethyl ester 150 ml and diethylamine 200 ml are heated to 60-70 degrees C. for 5 hours. The reaction mixture is evaporated at 50-60 degrees C. in vacuum to remove volatile materials. The residue thus obtained is mixed with 1 liter of cold water and the oily product is dried over anhydrous sodium sulfate. N,N-diethyl mandelic amide 125 g thus prepared is suitable for the following synthesis.

N,N-diethyl mandelic amide 75 g is dissolved in 200 ml of acetic anhydride and concentrated sulfuric acid 0.5 ml is added. The reaction mixture is heated to 90-100° for 3 hours to complete the acetylation. The mixture is then evaporated at 60-70° in vacuum to remove acetic acid and the like. The residue thus obtained is mixed with 1 liter of 5% sodium bicarbonate, and the oily product is extracted with 300 ml of chloroform. The chloroform layer is washed with 300 ml of 5% sodium bicarbonate and is dried over anhydrous sodium sulfate. On evaporation of chloroform solution a syrupy product 67 g is obtained.

N,N-diethyl phenyl-alpha-acetoxyacetamide thus synthesized is identified by infrared spectroscopy, high performance liquid chromatography and thin-layer chromatography with a mobility of 0.78 on a solvent system of benzene:methanol 1:1.

EXAMPLE 18

Synthesis of N-(3'-picolyl)phenyl-alpha-acetoxyacetamide

The following method may be applied to synthesis of all N-picolyl phenyl-alpha-acetoxyacetamides.

Mandelic acid ethyl ester 150 ml and 3-aminomethylpyridine 150 ml are mixed with stirring at room temperature for 5 hours. White crystalline product thus formed is washed with water and is dried at 50° C. in vacuum. N-(3'-picolyl)phenyl-alpha-hydroxyacetamide 165 g thus prepared is suitable for the following synthesis.

N-(3'-picolyl) phenyl-alpha-hydroxyacetamide 100 g is suspended in 200 ml of acetic anhydride and concentrated sulfuric acid 0.5 ml is added. The reaction mixture is heated to 80–90 degrees C. for 5 hours. During the initial stage of acetylation N-(3'-picolyl)phenyl-alpha-hydroxyacetamide dissolves at about 80 degrees C. and the acetylation takes place immediately with a change in color of the reaction mixture to a reddish solution. The reaction mixture is evaporated at 70–80 degrees C. in vacuum to remove acetic acid and the like. The residue is mixed with 1 liter of cold water and the syrupy product is extracted with 250 ml of chloroform. The chloroform layer is washed with 5% sodium bicarbonate 300 ml and is dried over anhydrous sodium sulfate. On evaporation of chloroform solution a syrupy product 98 g is obtained.

N-(3'-picolyl) phenyl-alpha-acetoxyacetamide thus synthesized is identified by infrared spectroscopy, high performance liquid chromatography and thin-layer chromatography with a mobility of 0.62 on a solvent system of benzene:methanol 1:1.

EXAMPLE 19

Synthesis of N-ethyl diphenyl-alpha-acetoxyacetamide

The following method may be applied to synthesis of all N-alkyl diphenyl-alpha-acetoxyacetamides.

Benzilic acid methyl ester 100 g is dissolved in 450 ml of methanol. Ethylamine 70% in water, 200 ml is added to the solution with stirring. After 2 days at room temperature the reaction mixture is evaporated at 40 degrees C. in vacuum to remove the volatile materials. The residue is mixed with 400 ml of cold water. White crystals thus formed are washed with water and dried. N-ethyl benzilic amide 95 g thus prepared is suitable for the following synthesis.

N-ethyl benzilic amide 83 g is dissolved in 150 ml of acetic anhydride and concentrated sulfuric acid 0.5 ml is added. The mixture is heated to 90–100 degrees C. for 3 hours to complete the acetylation. Cold water 2 liters is added to the reaction mixture, and the sticky solid is extracted with 250 ml of chloroform. The chloroform layer is washed with 300 ml of 5% sodium bicarbonate and is dried over anhydrous sodium sulfate. On evaporation of chloroform solution a syrupy product 79 g is obtained.

N-ethyl diphenyl-alpha-acetoxyacetamide thus synthesized is identified by infrared spectroscopy, high performance liquid chromatography and thin-layer chromatography with a mobility of 0.83 on a solvent system of benzene:methanol 1:1.

Alternatively, N-ethyl diphenyl-alpha-acetoxyacetamide may be synthesized by the following different method.

N-ethyl benzilic amide 51 g is dissolved in 200 ml of pyridine and acetyl chloride 24 ml is slowly added to the mixture with stirring and external cooling in an ice water bath. After 5 hours cold 0.2N HCL, one liter is added to the reaction mixture and the sticky solid is extracted with 200 ml of chloroform. The chloroform layer is washed with 300 ml of 5% sodium bicarbonate and is dried over anhydrous sodium sulfate. On evaporation of chloroform solution a syrupy product 43 g is obtained. N-ethyl diphenyl-alpha-acetoxyacetamide thus synthesized is identical to that prepared by the foregoing method.

EXAMPLE 20

Synthesis of N-phenethyl diphenyl-alpha-acetoxyacetamide

The following method may be applied to synthesis of all N-aralkyl diphenyl-alpha-acetoxyacetamides.

Benzilic acid methyl ester 200 g and phenethylamine 200 ml are heated to 50–60 degrees C. for 5 hours. White crystals formed after cooling are washed with water and are dried at 40 degrees C. in vacuum. N-phenethyl benzilic amide 225 g thus prepared is suitable for the following synthesis.

N-phenethyl benzilic amide 100 g is suspended in 200 ml of acetic anhydride and concentrated sulfuric acid 0.5 ml is added. The reaction mixture is heated to 90–100 degrees C. for 5 hours. Yellowish crystals 117 g formed during the cooling process are washed with water and are dried at 40 degrees C. in vacuum.

N-phenethyl diphenyl-alpha-acetoxyacetamide thus synthesized is identified by infrared spectroscopy, high performance liquid chromatograophy and thin-layer chromatography with a mobility of 0.82 on a solvent system of benzene:methanol 1:1.

EXAMPLE 21

For oral administration gelatin capsules containing phenyl-alpha-acyloxyacetamide derivatives in different doses may be prepared as follows.

N-ethyl phenyl-alpha-acetoxyacetamide powder 20 g is thoroughly mixed with 90 g of gelatin powder USP. Each gelatin capsule size No. 0 filled with this mixture contains 75 mg of N-ethyl phenyl-alpha-acetoxyacetamide as an active ingredient.

Gelatin capsules containing 150 mg of N-ethyl phenyl-alpha-acetoxyacetamide in each capsule may also be prepared in the same way but from 20 g of the active ingredient and 45 g of gelating powder.

EXAMPLE 22

Phenyl-alpha-acyloxyacetamide derivatives for parenteral injections may be prepared as follows.

N-phenethyl phenyl-alpha-acetoxyacetamide fine powder 0.2 g is suspended in 10 ml saline and the mixture in a sealed injection bottle is sterilized at 100 degrees C. for 20 minutes. The parenteral composition thus prepared contains 2% of active ingredient, i.e. 20 mg per ml of N-phenethyl phenyl-alpha-acetoxyacetamide.

EXAMPLE 23

A combination composition containing both a phenyl-alpha-acyloxyacetamide derivative and a corticosteroid may be formulated as follows. N-ethyl phenyl-alpha-acetoxyacetamide 3 g and hydrocortisone-17-valerate 0.2 g are dissolved in 10 ml of acetone, and the solution thus obtained is mixed with 88.9 g of hydrophilic ointment USP. Mixing is continued until a uniform consistency is obtained.

The therapeutic composition thus formulated contains 3% N-ethyl phenyl-alpha-acetoxyacetamide and 0.2% hydrocortisone-17-valerate as active ingredients.

EXAMPLE 24

Synthesis of N-isopropyl phenyl-alpha-acetoxyacetamide

Isopropylamine 20 ml is dissolved in 100 ml of ice water and O-acetylmandelic acid chloride 21 ml is added slowly to the solution with stirring. An oily substance is formed instantly in the bottom of the reaction flask during the addition of O-acetylmandelic acid chloride. After 10 minutes the oily substance is separated, dissolved in 100 ml of chloroform, washed with dilute HCl and dried over anhydrous sodium sulfate. On evaporation of the chloroform solution a syrupy product is obtained. N-isopropyl phenyl-alpha-acetoxyacetamide 18 g thus synthesized is identified by infrared spectroscopy, high performance liquid chromatography and thin-layer chromatography with a mobility of 0.81 on a solvent system of benzene:methanol 1:1.

EXAMPLE 25

Synthesis of N-t-butyl phenyl-alpha-acetoxyacetamide t-Butylamine 19 ml is dissolved in 120 ml of benzene and O-acetylmandelic acid chloride 20 ml is slowly added to the solution with stirring while the reaction flask is cooled externally with an ice water bath. White precipitates are formed instantly during the addition of O-acetylmandelic acid chloride. After two hours at room temperature the reaction mixture is mixed with 200 ml of cold water, and the benzene layer is separated, washed with dilute HCl and dried over anhydrous sodium sulfate. On evaporation of the benzene solution white crystals are formed, and the crystals are washed with n-hexane. N-t-Butyl phenyl-alpha-acetoxyacetamide 13 g thus synthesized is identified by infrared spectroscopy, high performance liquid chromatography and thin-layer chromatography with a mobility of 0.71 on a solvent system of benzene:methanol 1:1.

EXAMPLE 26

Synthesis of N-hydroxyethylthioethyl phenyl-alpha-acetoxyacetamide 2-((2-Aminoethyl)-thio) ethanol 25 ml is dissolved in 70 ml of chloroform and O-acetylmandelic acid chloride 20 ml is slowly added to the solution with stirring while the reaction flask is cooled externally with an ice water bath. After 3 hours at room temperature the reaction mixture is mixed with 200 ml of cold water, and the chloroform layer is separated, washed with dilute sodium bicarbonate, dilute HCl and dried over anhydrous sodium sulfate. On evaporation of the chloroform solution a syrupy product is obtained. N-Hydroxyethylthioethyl phenyl-alpha-acetoxyacetamide 21 g thus synthesized is identified by infrared spectroscopy, high performance liquid chromatography and thin-layer chromatography with a mobility of 0.64 on a solvent system of benzene:methanol 1:1.

EXAMPLE 27

Synthesis of N-(3,4-dimethoxyphenethyl) phenyl-alpha-acetoxyacetamide

Beta-(3,4-Dimethoxyphenyl)ethylamine 38 ml is dissolved in 120 ml of benzene and O-acetylmandelic acid chloride 20 ml is slowly added to the solution with stirring while the reaction flask is cooled externally with an ice water bath. White precipitates are formed instantly during the addition of O-acetylmandelic acid chloride. After one hour at room temperature the reaction mixture is mixed with 200 ml of cold water, and the benzene layer is separated, washed with dilute sodium bicarbonate, dilute HCl and dried over anhydrous sodium sulfate. The benzene solution is cooled externally with an ice water bath, and white crystals are formed. The crystals are washed with water and ether. N-(3,4-dimethoxyphenethyl) phenyl-alpha-acetoxyacetamide 33 g thus synthesized is identified by infrared spectroscopy, high performance liquid chromatography and TLC with a mobility of 0.82 on a solvent system of benzene:methanol 1:1.

EXAMPLE 28

Synthesis of N-P-chlorobenzyl phenyl-alpha-acetoxyacetamide

4-Chlorobenzylamine 30 ml is dissolved in 100 ml of chloroform and O-acetylmandelic acid chloride 20 ml is slowly added to the solution with stirring while the reaction flask is cooled externally with an ice water bath. White precipitates are formed instantly during the addition of O-acetylmandelic acid chloride. After one hour at room temperature the reaction mixture is mixed with 300 ml of cold water, and the chloroform layer is separated, washed with dilute sodium bicarbonate, dilute HCl and dried over anhydrous sodium sulfate. On evaporation of the chloroform solution white crystals are obtained. The crystals are washed with ether. N-P-Chlorobenzyl phenyl-alpha-acetoxyacetamide 28 g thus synthesized is identified by infrared spectroscopy, high performance liquid chromatography and thin-layer chromatography with a mobility of 0.77 on a solvent system of benzene:methanol 1:1.

EXAMPLE 29

Synthesis of N-P-methoxybenzyl phenyl-alpha-acetoxyacetamide

P-Methoxybenzylamine 29 ml is dissolved in 130 ml of chloroform and O-acetylmandelic acid chloride 20 ml is slowly added to the solution with stirring while the reaction flask is cooled externally with an ice water bath. White precipitates are formed instantly during the addition of O-acetylmandelic acid chloride. After one hour at room temperature the reaction mixture is mixed with 200 ml of cold water, and the chloroform layer is separated, washed with dilute HCl and dried over anhydrous sodium sulfate. On evaporation of the chloroform solution a syrupy residue is obtained. After trituration in dilute HCl the syrupy product becomes white crystals which are washed with ether. N-P-Methoxybenzyl phenyl-alpha-acetoxy acetamide 26 g thus synthesized is identified by infrared spectroscopy, high performance liquid chromatography and thin-layer chromatography with a mobility of 0.76 on a solvent system of benzene:methanol 1:1.

EXAMPLE 30

Synthesis of N-P-methoxyphenethyl phenyl-alpha-acetoxyacetamide

P-Methoxyphenethylamine 30 ml is dissolved in 150 ml of chloroform and O-acetylmandelic acid chloride 20 ml is slowly added to the solution with stirring while the reaction flask is cooled externally with an ice water bath. White precipitates are formed instantly during the addition of O-acetylmandelic acid chloride. After 3 hours at room temperature the reaction mixture is mixed with 300 ml of cold water, and the chloroform layer is separated, washed with dilute HCl and dried over anhydrous sodium sulfate. On evaporation of the chloroform solution a syrupy residue is obtained. After cooled in an ice water bath the syrupy residue becomes a crystalline product. The crystals are washed with ether. N-P-methoxyphenethyl phenyl-alpha-acetoxyacetamide 21 g thus synthesized is identified by infrared spectroscopy, high performance liquid chromatography and thin-layer chromatography with a mobility of 0.66 on a solvent system of benzene:methanol 1:1.

EXAMPLE 31

A combination composition containing both a phenyl-alpha-acyloxyacetamide derivative and an anti-inflammatory corticosteroid may be formulated as follows. N-Benzyl phenyl-alpha-acetoxyacetamide 5 g and triamcinolone acetonide 0.1 g are dissolved in 7 ml of acetone, and the solution thus obtained is mixed with 88 g of hydrophilic ointment USP. Mixing is continued until a uniform consistency is obtained.

The therapeutic composition thus formulated contains 5% N-benzyl phenyl-alpha-acetoxyacetamide and 0.1% triamcinolone acetonide as active ingredients.

EXAMPLE 32

A combination composition containing both a phenyl-alpha-acyloxyacetamide derivative and an antiparasitic lindane, gamma benzene hexachloride may be formulated as follows. N-Phenethyldiphenyl-alpha-acetoxyacetamide 3 g and lindane 1 g are dissolved in 10 ml of acetone, and the solution thus obtained is mixed with 86 g of hydrophilic ointment USP. Mixing is continued until a uniform consistency is obtained.

The therapeutic composition thus formulated contains 3% N-phenethyl diphenyl-alpha-acetoxy-acetamide and 1% lindane as active ingredients.

EXAMPLE 33

A combination composition containing both a phenyl-alpha-acyloxyacetamide derivative and an anti-fungal agent, clotrimazole, may be formulated as follows. N-P-chlorobenzyl phenyl-alpha-acetoxyacetamide 4 g and clotrimazole 1 g are dissolved in 10 ml of acetone, and the solution thus obtained is mixed with 85 g of hydrophilic ointment USP. Mixing is continued until a uniform consistency is obtained.

The therapeutic composition thus formulated contains 4% N-P-chlorobenzyl phenyl-alpha-acetoxyacetamide and 1% clotrimazole as active ingredients.

EXAMPLE 34

A combination composition containing antipruritic, anti-inflammatory and antibiotic agents may be formulated as follows. Finely powdered N-(3,4-dimethoxyphenethyl) phenyl-alpha-acetoxyacetamide 3 g, triamcinolone acetonide 0.1 g, neomycin sulfate 0.5 g and polymyxin B sulfate 0.05 g are directly mixed with 97 g of hydrophilic ointment USP. Mixing is continued until a uniform consistency is obtained.

The therapeutic composition thus formulated contains four active ingredients: N-(3,4-dimethoxyphenethyl)phenyl-alpha-acetoxyacetamide 3%, triamcinolone acetonide 0.1%, Neomycin sulfate 0.5%, and polymyxin B sulfate 0.05%.

ANIMAL STUDIES

(1) ACUTE AND SUBACUTE TOXICITY

Twenty mice were given each phenyl-alpha-acyloxyacetamide derivative as single subcutaneous injections at various doses. It was found that all the phenyl-alpha-acyloxyacetamide derivatives tested at doses up to 400 mg/kg were nontoxic, i.e. all mice were alive and healthy at the end of 5 weeks after the administration of the substance. The $LD_{50}$ of each phenyl-alpha-acyloxyacetamide derivative was found to be higher than 1 g/kg.

(2) CHRONIC TOXICITY

Twenty mice were given each phenyl-alpha-acyloxyacetamide derivative subcutaneously twice weekly in doses of 80 mg/kg for 3 months. It was found that phenyl-alpha-acyloxyacetamide derivative in a total dose of 1,920 mg/kg given over such 3 month periods were nontoxic for mice.

(3) SCREENING COMPOUNDS FOR ANTI-PRURITIC EFFECT

(A) Topical Application

Either the mouse or the rat may be used as a screening model for anti-pruritic compounds. Before testing hair is plucked from the test site of skin in haired animals. Therefore hairless strains of mouse or the strain of rat known as fuzzy rat is preferred as a screening model for the present purpose.

A test composition containing 5% phenyl-alpha-acyloxyacetamide derivative in solution was topically applied to the left dorsal skin of a hairless mouse and a control vehicle solution was topically applied to the right dorsal skin of the same mouse. The same topical applications were repeated three times at 30 minute intervals. A challenging composition containing a pruritic agent, i.e. itch provoking substance, was then topically applied in a volume of 0.05 ml on both left and right dorsal skin of the same mouse. For the next 30 minutes the mouse was carefully observed for signs and symptoms of scratching or licking at the skin sites where the challenging pruritic composition had been topically applied.

If the mouse scratched or licked indiscriminately at both left and right sides, the test composition was determined to have no anti-pruritic property. On the other hand if the mouse scratched or licked only the right side of the skin and did not scratch or lick, or did so minimally the left side of the skin, the test composition was determined to have an anti-pruritic effect. To confirm the anti-pruritic effect of the test composition, the test solution was later topically applied to the right instead of the left dorsal skin of the same mouse. The same topical applications were repeated three times at 30 minute intervals. A challenging composition containing the same pruritic agent was then topically applied on the right dorsal skin site of the same mouse. If the mouse did not scratch or lick, or did so minimally, the right test site of the skin, the test composition was confirmed to have anti-pruritic effect.

Occasionally, a mouse might not scratch or lick either side of the dorsal skin following topical application of a pruritic composition on both sides of the dorsal skin although only the left side of the dorsal skin had been topically treated with an anti-pruritic composition. This situation might conceivably arise when an anti-pruritic compound in the composition topically applied on the left side of mouse skin had been substantially absorbed through the skin and had thus exerted its systemic anti-pruritic effect. To eliminate such possibilities a different mouse instead of the same mouse is used as a control study. At least two mice were used to screen anti-pruritic effect of each phenyl-alpha-acyloxyacetamide derivative.

We have found that the phenyl-alpha-acyloxyacetamide derivatives which include N-ethyl phenyl-alpha-acetoxyacetamide and N-phenethyl phenyl-alpha-acetoxyacetamide tested by the above screening method showed a substantial anti-pruritic effect.

(B) Systemic Administration

Either the mouse or the rat may be used as a screening model for anti-pruritic compounds. Again, the hairless mouse or the fuzzy rat is a preferred strain in each species.

A test composition in a volume of 0.1 ml containing 5% phenyl-alpha-acyloxyacetamide derivative in solution was injected subcutaneously to the hairless mouse. The same procedure was repeated once more 3 hours later. Two hours after the second injection the mouse was challenged with a pruritic composition either applied topically or administered subcutaneously. When the challenging composition containing a pruritic agent was given topically the solution in a volume of 0.05 ml was applied to the left dorsal skin. A control vehicle solution containing no pruritic agent in the same volume of 0.05 ml was topically applied on the right dorsal skin. For the next 30 minutes the mouse was carefully observed for signs and symptoms of scratching or licking at the skin sites where the pruritic composition and the control vehicle solution had been topically applied.

If the mouse scratched or licked only the left side of the skin where the pruritic composition had been topically applied the test composition which was injected subcutaneously at two and five hours earlier was determined to have no anti-pruritic property. If the mouse did not scratch nor lick, or did so minimally at both the left and the right side of the skin, the test composition which was injected subcutaneously at two and five hours earlier was determined to have anti-pruritic effect.

When the challenging composition containing a pruritic agent was administered subcutaneously the pruritic solution in a volume of 0.1 ml was injected in the left dorsal skin and the control vehicle solution in the same volume was injected in the right doral skin. For the next 30 minutes the mouse was carefully observed for signs and symptoms of scratching or licking the skin sites where the pruritic composition and the control vehicle solution had been injected subcutaneously. The criteria for determination of anti-pruritic or non-antipruritic effect of the test composition were the same as described in the foregoing. At least two mice were used to screen anti-pruritic effect of each phenyl-alpha-acyloxyacetamide derivative.

We have found that the phenyl-alpha-acyloxyacetamide derivatives which include N-ethyl phenyl-alpha-acetoxyacetamide and N-phenethyl phenyl-alpha-acetoxyacetamide tested by the above screening method showed a substantial anti-pruritic effect.

ANTI-PRURITIC EFFECT ON NORMAL HUMAN SKIN

Itch provoking pruritic compositions were prepared as follows: papain 0.5% solution was prepared by dissolving papain 50 mg in 10 ml of saline, and histamine 0.2% solution was prepared by dissolving histamine dihydrochloride 20 mg in 10 ml of saline. Itching was provoked or induced as follows: a pruritic composition in a volume of 0.05 ml containing papain or histamine dihydrochloride as a pruritic agent was topically applied on the flexor forearm of normal human adult volunteers and the skin site was gently pricked rapidly through the solution with a 26-gauge needle to the level of the papillary dermis as described by Bernstein et al. (J. E. Bernstein, R. M. Swift, K. Soltani and A. L. Lorincz: Antipruritic Effect of an Opiate Antagonist, Naloxone Hydrochloride in Journal of Investigative Dermatology 78, 82–83, 1982). This technique provoked or induced itch sensation at the test skin site within a few minutes following the topical application of the pruritic composition. After itch sensation had been induced a composition containing 2 to 5% N-ethyl phenyl-alpha-acetoxyacetamide, N-phenethyl phenyl-alpha-acetoxyacetamide or other phenyl-alpha-acyloxyacetamide derivatives of the instant invention was topically applied on the pruritic skin site. The vehicle alone cream containing no active ingredient was used as a control.

We have found that the composition containing N-ethyl phenyl-alpha-acetoxyacetamide, N-phenethyl phenyl-alpha-acetoxyacetamide, N-phenethyl diphenyl-alpha-acetoxyacetamide or other phenyl-alpha-acyloxyacetamide derivative tested by the above screening method showed a substantial anti-pruritic effect. The vehicle alone cream did not show any anti-pruritic effect.

PRURITUS

Patients with various kinds of pruritic disorders participated in this study. The cases included atopic eczema, patchy eczema, chronic eczema of the hands, lichen simplex chronicus, contact allergic eczema, pruritus of the aged, pruritus of hepatic origin, pruritus ani, pruritus vulvae, scalp pruritus and pruritus of other disorders such as mycosis fungoides, psoriasis and pityriasis rubra pilaris.

Therapeutic compositions containing phenyl-alpha-acyloxyacetamides at 2 to 5% concentrations in cream, ointment, lotion or solution were prepared according to the Examples. The medicinal compositions were topically applied by the patient in an amount sufficient to cover the itching area of skin. Applications were made one to two times daily or as frequently as necessary and without occlusive dressings.

The therapeutic compositions containing phenyl-alpha-acyloxyacetamides provided the anti-pruritic effect after a few minutes to a few hours, depending on the active ingredient and some variability in degree of response among patients following topical application. In general, however, the therapeutic compositions of the instant invention exerted their anti-pruritic effect rather promptly following topical administration.

Two parameters have been used to compare degrees of anti-pruritic effect of phenyl-alpha-acyloxyacetamides. The first parameter is whether the relief of itching is complete (2+) or incomplete (1+). The second parameter is the number of hours the patient stays free of pruritus after the initial anti-pruritic effect. Most phenyl-alpha-acyloxyacetamides give 8 to more than 24 hours (2+) of complete relief from itching; some compounds provide less than 8 hours (1+) of relief from pruritus. Therefore, the overall anti-pruritic effect of a compound may range from 2+ to 4+. For example, the anti-pruritic effect is 2+ when a compound gives an incomplete relief from itching and lasts for less than 8 hours; 3+ for either complete relief but lasting for less than 8 hours or incomplete relief but lasting for more than 8 hours. 4+ for complete relief and lasting for more than 8 hours.

The test results are summarized on the following tables.

Topical Anti-pruritic Effect of the
First Category of Phenyl-alpha-acyloxyacetamides
on Eczemas, and Other Pruritic Disorders

| Compounds | Number of Patients | Anti-pruritic Effect |
|---|---|---|
| 1. N—ethyl phenyl-alpha-acetoxyacetamide | 14 | 4+ |
| 2. N—phenethyl phenyl-alpha acetoxyacetamide | 16 | 4+ |
| 3. N—benzyl phenyl-alpha-acetoxyacetamide | 19 | 4+ |
| 4. N—ethyl phenyl-alpha phenylacetoxy acetamide | 6 | 4+ |
| 5. N,N—diethyl phenyl-alpha-acetoxyacetamide | 5 | 4+ |
| 6. N—phenethyl phenyl-alpha-propionyloxyacetamide | 2 | 3+ |
| 7. N—methyl phenyl-alpha-acetoxyacetamide | 3 | 3+ |
| 8. N—t-butyl phenyl-alpha-acetoxyacetamide | 4 | 4+ |
| 9. N—isopropyl phenyl-alpha-acetoxyacetamide | 3 | 3+ |
| 10. N—P—chlorobenzyl phenyl-alpha-acetoxyacetamide | 3 | 4+ |
| 11. N—P—methoxybenzyl phenyl-alpha-acetoxyacetamide | 4 | 4+ |
| 12. N—P—methoxyphenethyl phenyl-alpha-acetoxyacetamide | 4 | 4+ |
| 13. N—(3,4-dimethoxyphenethyl) phenyl-alpha acetoxyacetamide | 5 | 4+ |
| 14. N,N—dibenzyl phenyl-alpha-acetoxyacetamide | 3 | 3+ |
| 15. N—hydroxyethylthioethyl phenyl-alpha-acetoxyacetamide | 4 | 3+ |

As shown by the above table, ten phenyl-alpha-acyloxyacetamide derivatives completely abolished itch sensations for more than 8 hours in all the patients tested. The remaining five phenyl-alpha-acyloxyacetamide derivatives completely abolished itch sensations but the anti-pruritic effect lasted for only 4 to 7 hours.

Topical Anti-pruritic Effect of the
Second Category of Phenyl-alpha-acyloxyacetamides
on Eczemas and Other Pruritic Disorders

| Compounds | Number of Patients | Anti-pruritic Effect |
|---|---|---|

As shown by the above table, six phenyl-alpha-acyloxyacetamide derivatives completely abolished itch sensations for more than 8 hours in all the patients tested. N-phenethyl diphenyl-alpha-propionyloxyacetamide also completely abolished itch sensations but the anti-pruritic effect lasted for less than 8 hours.

Topical Anti-pruritic Effect of the
Intermediate and Related Compounds on
Eczemas and Other Pruritic Disorders

| Compounds | Number of Patients | Anti-pruritic Effect |
|---|---|---|
| 1. N—ethyl phenyl-alpha-hydroxyacetamide | 4 | 2+ |
| 2. N—phenethyl phenyl-alpha hydroxyacetamide | 3 | 3+ |
| 3. N—benzyl phenyl-alpha-hydroxyacetamide | 3 | 2+ |
| 4. N—methyl phenyl-alpha-hydroxyacetamide | 2 | 2+ |
| 5. N—3'-picolyl phenyl-alpha-hydroxyacetamide | 2 | 2+ |
| 6. N—3'-picolyl phenyl-alpha-acetoxyacetamide | 2 | 3+ |
| 7. N—(N',N'-diethylaminoethyl)phenyl-alpha-hydroxyacetamide | 2 | 2+ |
| 8. N—(N',N'-diethylaminoethyl)phenyl-alpha-acetoxyacetamide | 2 | 3+ |
| 9. N—phenethyl phenyl-alpha-(0-acetylmandeloyloxy)-acetamide | 2 | 3+ |

As noted by the above table, the intermediate and related compounds of phenyl-alpha-acyloxyacetamide derivatives showed various degrees of anti-pruritic effect in all the patients tested.

Topical Antipruritic and Anti-inflammatory Effects
of Combination Compositions on Poison Ivy Dermatitis,
Insect Bite Reactions, Sea Nettle Sting Reactions
and Other Like Conditions

| Compositions | Number of Subjects | Anti-pruritic Effect | Anti-Inflammatory Effect |
|---|---|---|---|
| 1. N—benzyl phenyl-alpha-acetoxyacetamide and triamcinolone acetonide | 3 | 4+ | 4+ |
| 2. N—Phenethyl phenyl-alpha-acetoxyacetamide and hydrocortisone-17-valerate | 2 | 4+ | 4+ |
| 3. N—Phenethyl diphenyl-alpha-acetoxyacetamide and hydrocortisone-21-acetate | 3 | 4+ | 4+ |
| 4. N—(N',N'-diethylaminoethyl) diphenyl-alpha-acetoxy-acetamide and hydrocortisone | 2 | 4+ | 4+ |

As shown by the above table, all the combination compositions completely abolished itch sensations from poison ivy contacts and mosquito bites, the stinging sensation from sea nettle contacts and other like conditions from environmental contacts and also substantially improved the appearance of the affected area of the skin.

Topical Antipruritic and Anti-fungal Effects of
Combination Compositions on Fungal Infections of the Skin

| Compositions | Number of Subjects | Anti-pruritic Effect | Anti-fungal Effect |
|---|---|---|---|
| 1. N—phenethyl phenyl-alpha-acetoxyacetamide and clotrimazole | 3 | 4+ | 4+ |

| Topical Antipruritic and Anti-fungal Effects of Combination Compositions on Fungal Infections of the Skin |||| 
|---|---|---|---|
| Compositions | Number of Subjects | Anti-pruritic Effect | Anti-fungal Effect |
| 2. N—Benzyl phenyl-alpha-acetoxyacetamide and clotrimazole | 2 | 4+ | 4+ |
| 3. N—phenethyl diphenyl-alpha acetoxyacetamide and miconazole | 2 | 4+ | 4+ |
| 4. N—Ethyl phenyl-alpha-acetoxyacetamide and miconazole | 3 | 4+ | 4+ |

As shown by the above table, all the combination compositions completely abolished itch sensations from fungal infections, and also eradicated such infections.

| Topical Antipruritic and Antiparasitic Effects of Combination Compositions on Pediculosis and Scabies Infestations ||||
|---|---|---|---|
| Compositions | Number of Patients | Anti-pruritic Effect | Anti-Parasitic Effect |
| 1. N—P—chlorobenzyl phenyl-alpha-acetoxyacetamide and lindane | 2 | 4+ | 4+ |
| 2. N—phenethyl diphenyl-alpha acetoxyacetamide and lindane | 2 | 4+ | 4+ |

As shown by the above table, all the combination compositions completely abolished itch sensations from lice and mites, and also successfully eradicated such infestations.

| Topical Antipruritic and Anti-infectious Effects of Combination Compositions on Bacterial, Viral and Yeast Infections ||||
|---|---|---|---|
| Compositions | Number of Patients | Anti-pruritic Effect | Anti-Infectious Effect |
| 1. N—P—methoxyphenethyl phenyl-alpha-acetoxyacetamide, neomycin and polymyxin B | 2 | 4+ | 4+ |
| 2. N—p-fluorobenzyl phenyl-alpha-acetoxyacetamide, neomycin, polymyxin B and triamcinolone acetonide | 3 | 4+ | 4+ |

As shown by the above table, all the combination compositions effectively abolished itch sensations from various infections, and also successfully eradicated such infections.

SYSTEMIC ADMINISTRATION

Three dogs with summer eczema-prurigo were treated with oral administration of phenyl-alpha-acyloxyacetamide derivatives. Gelatin capsules containing N-ethyl phenyl-alpha-acetoxyacetamide or N-phenethyl phenyl-alpha-acetoxyacetamide at dosages ranging from 50 mg to 150 mg per capsule were prepared according to Examples. Single doses of 5 mg/kg to 10 mg/kg were administered orally to the dogs.

All three dogs stopped scratching within one hour following oral administration of N-ethyl phenyl-alpha-acetoxyacetamide or N-phenethyl phenyl-alpha-acetoxyacetamide. This anti-scratch or anti-pruritic effect lasted for approximately 8 hours. Following the oral administration of N-ethyl phenyl-alpha-acetoxyacetamide or N-phenethyl phenyl-alpha-acetoxyacetamide, all three dogs were mentally alert as usual and did not have any signs or symptoms of drowsiness or intoxication.

Oral doses containing N-ethyl phenyl-alpha-acetoxyacetamide or N-phenethyl phenyl-alpha-acetoxyacetamide were administered repeatedly to the dogs at intervals of two to several days. Each time the phenyl-alpha-acyloxyacetamide derivative provided the same anti-pruritic or anti-scratching effect. No evidence of adverse effects was detected.

The foregoing results suggest and imply that members of phenyl-alpha-acyloxyacetamide derivatives are predictably useful as systemic anti-pruritic agents for treatment of humans as well as animals with dermatologic conditions or diseases associated with itching.

TRANQUILIZING EFFECTS

1. Topical Administration

Hairless mice, ten in each group, were used in this study. N-phenethyl phenyl-alpha-acetoxyacetamide, N-ethyl phenyl-alpha-acetoxyacetamide or other phenyl-alpha-acyloxyacetamide derivative of the instant invention was prepared as a 5% solution in acetone:water, 8:2 or ethanol:water, 8:2. A test solution was topically applied to the left dorsal skin of hairless mice. The same topical applications were repeated three times at 30 minute intervals. A vehicle alone solution containing acetone and water or ethanol and water was used as a control. For the next 8 hours and also 24 hours later all mice were carefully observed and examined for any signs or evidence of calming or quieting effects caused by the test compound.

Normally when a mouse is picked up by the tail with thumb and forefinger the mouse struggles trying to free itself; and if the mouse is placed on a horizontal metallic grid uniformly spaced at 8 mm, the mouse nervously pulls itself across the grid, again trying to free itself from the restraining grip of the fingers.

If during the above observation period the mouse behaved the same before and after the topical treatment when picked up by the tail and placed on the metallic grid, the test compound was determined to have no significant tranquilizing effect by topical administration. On the other hand, if the mouse was calm and quiet after the topical treatment when picked up by the tail and also did not struggle on the metallic grid, the test compound was determined to have a tranquilizing or sedative effect.

We have found that phenyl-alpha-acyloxyacetamide derivatives of the instant invention on topical administration showed various degrees of tranquilizing action, from minimally detectable to marked effects. For example, whereas N-ethyl phenyl-alpha-acetoxyacetamide exerted no detectable signs of sedation, N-phenethyl phenyl-alpha-acetoxyacetamide showed marked degrees of tranquilizing effect after topical administration.

2. Systemic Administration

Hairless mice, white hairy mice and dogs were used in these studies.

N-phenethyl phenyl-alpha-acetoxyacetamide, N-ethyl phenyl-alpha-acetoxyacetamide or other phenyl-alpha-acyloxyacetamide derivative of the instant invention was prepared as a 1 to 2% solution or as gelatin capsules containing 75 to 300 mg per capsule of the active ingredient. Hairless mice or white hairy mice five in each group were injected subcutaneously with the test solution in a volume of 0.1 ml. The same procedure was repeated once more 3 hours later. For the next 8 hours and also at 24 hours later, all the mice were carefully observed and examined for any signs and evidences of calming or quieting effects caused by the test compound.

Parameters and criteria used for sedative or tranquilizing effect were the same as that described in the foregoing section. We have found that phenyl-alpha-acyloxyacetamide derivatives of the instant invention on subcutaneous administration to mice showed various degrees from minimally detectable to marked effect of tranquilizing action. For example, whereas N-ethyl phenyl-alpha-acetoxyacetamide exerted no detectable signs of sedation N-phenethyl phenyl-alpha-acetoxyacetamide showed marked degrees of calming effect after subcutaneous administration to the mouse.

Three dogs weighing between 10 to 20 kg were given orally N-phenethyl phenyl-alpha-acetoxyacetamide or N-ethyl phenyl-alpha-acetoxyacetamide in gelating capsules at doses of 5 to 10 mg per kg. For the next 10 hours the dogs were carefully observed and examined for any signs or evidence of calming or sedative effects caused by the test compound.

We have found that whereas N-ethyl phenyl-alpha-acetoxyacetamide exerted no detectable signs of sedation N-phenethyl phenyl-alpha-acetoxyacetamide showed mild tranquilizing effect on oral administration to dogs. No soporific or drowsy effects have been detected in these dogs after oral administration of phenyl-alpha-acyloxyacetamide derivatives of the instant invention. In comparative studies these dogs at different times were given orally known tranquilizers such as Valium and antihistamine drugs such as Benadryl. Whereas known tranquilizers and antihistamine drugs exerted substantial sedative effects on the dogs on oral administration, these known drugs also caused soporific and drowsy effects in the dogs.

The foregoing results suggest and imply that members of phenyl-alpha-acyloxyacetamide derivatives are predictably useful as tranquilizers for treatment of anxiety or mental tension in humans, as well as animals.

ANALGESIC EFFECTS

To test whether in addition to tranquilizing effects in animals, analgesic properties of phenyl-alpha-acyloxyacetamide derivatives of the instant invention might exist we administered systemically these compounds to dogs. N-ethyl phenyl-alpha-acetoxyacetamide or N-phenethyl phenyl-alpha-acetoxyacetamide in single oral doses of approximately 8 mg per kg was given to two dogs disabled with hind limb arthritis secondary to hip dysplasia. One dog weighed 23 kg; the other weighed 28 kg.

The disability in both animals was such that they were unable to jump up upon a test table, 45 cm L×45 cm W×45 cm H, on which had been placed a piece of food as an inducement; nor were they able to run about or romp, their movements being limited to walking with evident stiffness of gait.

Two to three hours after oral administration of the N-ethyl phenyl-alpha-acetoxyacetamide or the N-phenethyl phenyl-alpha-acetoxyacetamide the physical incapacities of these dogs were observed to have been diminished.

Walking was improved and the animals would then trot with some ease. Both were able to jump up upon the table to claim the food placed thereupon.

The foregoing results suggest and imply that members of phenyl-alpha-acyloxyacetamide derivatives are predictably useful as analgesic agents for treatment of various aches, pains and discomforts of skin, joints and other body parts in humans, as well as animals.

PSORIASIS

The involved skin in psoriasis is hyperplastic (thickened); erythematous (red or inflamed), and has thick adherent scales. The degree of thickening is such that lesions are elevated up to 1 mm above the surface of adjacent normal skin; erythema is usually an intense red; the thickened adherent scales cause the surface of involved skin to be markedly rough and uneven. These three attributes of thickness, color and texture can be quantified to allow objective measurement of degree of improvement from topically applied therapeutic test materials as follows:

|  | Degree of Improvement | | | | |
| --- | --- | --- | --- | --- | --- |
|  | None (± to 0) | Mild (1− to 1+) | Moderate (2− to 2+) | Substantial (3− to 3+) | Complete (4− to 4+) |
| Thickness | Highly elevated | Detectable reduction | Readily apparent | Barely elevated | Normal thickness |
| Texture | Visibly rough | Palpably rough | Uneven but not rough | Slightly uneven | Visibly & palpably smooth |
| Color | Intense red | Red | Dark Pink | Light Pink | Normal color |

By means of such parameters degree of change in lesion can be numerically noted and comparisons made of one treated site to another.

Patients having psoriasis participated in this study. Therapeutic compositions containing phenyl-alpha-acyloxyacetamide derivatives were prepared according to the Examples. Test areas were kept to minimal size convenient for topical application, i.e. circles approximately 4 cm in diameter. The medicinal creams were topically applied by the patient in an amount (usually about 0.1 milliliter) sufficient to cover the test site. Applications were made two to three times daily and without occlusive dressings. Test periods did not exceed two weeks.

The following table summarizes the results of those tests:

| Effects on Psoriasis of Topical Phenyl-alpha-acyloxyacetamide Derivatives and Related Compounds | | |
|---|---|---|
| Compounds | No. of Patients | Therapeutic Effectiveness |
| 1. N—ethyl phenyl-alpha-acetoxyacetamide | 2 | 2+ |
| 2. Phenyl-alpha-hydroxyacetamide | 2 | 2+ |
| 3. N,N—diethyl phenyl-alpha hydroxyacetamide | 2 | 2+ |
| 4. N—methyl phenyl-alpha-hydroxyacetamide | 1 | 1+ |
| 5. N—ethyl phenyl-alpha-hydroxyacetamide | 1 | 1+ |
| 6. N—phenethylphenyl-alpha-acetoxyacetamide | 2 | 2+ |
| 7. N—benzyl phenyl-alpha-acetoxyacetamide | 2 | 3+ |
| 8. N—ethyl phenyl-alpha phenylacetoxyacetamide | 3 | 3+ |
| 9. N—(3,4-dimethoxyphenethyl) phenyl-alpha-acetoxyacetamide | 3 | 3+ |

The invention may be embodied in other specific forms without departing from the spirit or essential characteristics thereof. The present embodiments are therefore to be considered in all respects as illustrative and not restrictive, the scope of the invention being indicated by the appended claims and all changes which come within the meaning and equivalency of the claims are therefore intended to be embraced therein.

We claim:

1. A therapeutic composition comprising an antipruritic or antiinflammatory effective amount of a phenyl-alpha-acyloxyacetamide compound having the formula:

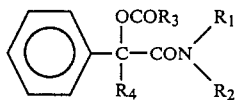

wherein
$R_1$, $R_2$=H, alkyl or aralkyl group of saturated or unsaturated, straight or branched chain or cyclic form, having 1 to 25 carbon atoms, $R_3$=alkyl, aralkyl or aryl group of saturated or unsaturated, straight or branched chain or cyclic form, having 1 to 25 carbon atoms;

$R_4$=H, alkyl, aralkyl or aryl group of saturated or unsaturated, straight or branched chain or cyclic form, having 1 to 25 carbon atoms; and the hydrogen atom of the phenyl, $R_1$, $R_2$, $R_3$ or $R_4$ may be substituted by a nonfunctional halogen or a radical such as a lower alkyl or alkoxy having 1 to 9 carbon atoms; and the carbon atom of $R_1$ or $R_2$ may be substituted by a nonfunctional N, S or O, in a pharmaceutically acceptable vehicle for topical application to involved body areas or internal administration.

2. The phenyl-alpha-acyloxyacetamide compound of claim 1 wherein the compound is a member selected from the group consisting of:
N-ethyl phenyl-alpha-acetoxyacetamide
N-phenethyl phenyl-alpha-acetoxyacetamide
N-ethyl phenyl-alpha-phenylacetoxyacetamide
N-phenethyl phenyl-alpha-phenylacetoxyacetamide
N-ethyl phenyl-alpha-benzoyloxyacetamide
N-allyl phenyl-alpha-acetoxyacetamide
N-ethyl phenyl-alpha-lauroyloxyacetamide
N-phenethyl phenyl-alpha-linoleoyloxyacetamide
N-phenethyl phenyl-alpha-linolenoyloxyacetamide
N-isopropyl phenyl-alpha-acetoxyacetamide
N-t-butyl phenyl-alpha-acetoxyacetamide
N-p-chlorobenzyl phenyl-alpha-acetoxyacetamide
N-p-methoxybenzyl phenyl-alpha-acetoxyacetamide
N-p-methoxyphenethyl phenyl-alpha-acetoxyacetamide
N-benzyl phenyl-alpha-acetoxyacetamide
N-(3,4-dimethoxyphenethyl) phenyl-alpha-acetoxyacetamide
N-(N',N'-diethylaminoethyl) phenyl-alpha-acetoxyacetamide
N-hydroxyethylthioethylphenyl-alpha-acetoxyacetamide
N-(2-phenylethanol) phenyl-alpha-acetoxyacetamide
N,N-dibenzyl phenyl-alpha-acetoxyacetamide
N-hydroxyethoxyethyl phenyl-alpha-acetoxyacetamide
N-diphenylmethyl phenyl-alpha-acetoxyacetamide
N-p-fluorobenzyl phenyl-alpha-acetoxyacetamide
N-p-methylbenzyl phenyl-alpha-acetoxyacetamide
N-p-chlorophenethyl phenyl-alpha-acetoxyacetamide
N-phenylpropyl phenyl-alpha-acetoxyacetamide; and
N-phenylbutyl phenyl-alpha-acetoxyacetamide.

3. The phenyl-alpha-acyloxyacetamide compound of claim 1 wherein the compound is a member selected from the group consisting of:
N-ethyl-diphenyl-alpha-acetoxyacetamide
N-phenethyl diphenly-alpha-acetoxyacetamide
N-ethyl diphenyl-alpha-phenylacetoxyacetamide
N-phenethyl diphenyl-alpha-phenylacetoxyacetamide
N-isopropyl diphenyl alpha-acetoxyacetamide
N-t-butyl diphenyl alpha-acetoxyacetamide
N-benzyl diphenyl-alpha-acetoxyacetamide
N-allyl diphenyl-alpha-acetoxyacetamide
N,N-diethyl diphenyl-alpha-acetozyacetamide
N-(N',N'-diethylaminoethyl) diphenyl-alpha-acetoxyacetamide
N-P-chlorobenzyl diphenyl-alpha-acetoxy-acetamide
N-P-methoxybenzyl diphenyl-alpha-acetoxy-acetamide
N-P-methoxyphenethyl diphenyl-alpha-acetoxyacetamide
N-(N',N'-diethylaminopropyl) diphenyl-alpha-acetoxyacetamide
N-(N',N'-dimethylamino propyl) diphenyl-alpha-acetoxyacetamide
N-p-fluorobenzyl diphenyl-alpha-acetoxyacetamide
N-p-methylbenzyl diphenyl-alpha-acetoxyacetamide
N-p-chlorophenethyl diphenyl-alpha-acetoxyacetamide
N-phenylpropyl diphenyl-alpha-acetoxyacetamide; and
N-phenylbutyl diphenyl-alpha-acetoxyacetamide.

4. A therapeutic composition comprising, in combination, an antipruritic, or antiinflammatory-enhancing effectice amount of a phenyl-alpha-acyloxyacetamide compound having the formula:

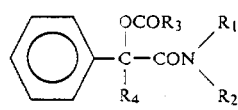

wherein:
$R_1$, $R_2$=H, alkyl or aralkyl group of saturated or unsaturated, straight or branched chain or cyclic form, having 1 to 25 carbon atoms, R3=aralkyl or aryl group of saturated or unsaturated, straight or branched chain or cyclic form, having 1 to 25 carbon atoms;

R4=H, alkyl, aralkyl or aryl group of saturated or unsaturated, straight or branched chain or cyclic form, having 1 to 25 carbon atoms; and the hydrogen atom of the phenyl, $R_1$, $R_2$, $R_3$ or $R_4$ may be substituted by a nonfunctional halogen or a radical such as a lower alkyl or alkoxy having 1 to 9 carbon atoms; and the carbon atom of $R_1$ or $R_2$ may be substituted by a nonfunctional N, S or O; an effective amount a dermatologic agent effective as an antiyeast, antifungal, antibacterial, antiviral, antiinflammatory, keratolytic, antipsoriatic, or antieczematic agent in a pharmaceutically acceptable vehicle for topical application to involved body areas or internal administration.

5. The phenyl-alpha-acyloxyacetamide compound of claim 4 wherein the compound is a member selected from the group consisting of:

N-ethyl phenyl-alpha-acetoxyacetamide
N-phenethyl phenyl-alpha-acetoxyacetamide
N-ethyl phenyl-alpha-phenylacetoxyacetamide
N-phenethyl phenyl-alpha-phenylacetoxyacetamide
N-benzyl phenyl-alpha-acetoxyacetamide
N-ethyl phenyl-alpha-benzoyloxyacetamide
N-allyl phenyl-alpha-acetoxyacetamide
N-ethyl phenyl-alpha-lauroyloxyacetamide
N-phenethyl phenyl-alpha-linoleoyloxyacetamide
N-phenethyl phenyl-alpha-linolenoyloxyacetamide
N-isopropyl phenyl-alpha-acetoxyacetamide
N-t-butyl phenyl-alpha-acetoxyacetamide
N-p-chlorobenzyl phenyl-alpha-acetoxyacetamide
N-p-methoxybenzyl phenyl-alpha-acetoxyacetamide
N-p-methoxyphenethyl phenyl-alpha-acetoxyacetamide
N-(3,4-dimethoxyphenethyl) phenyl-alpha-acetoxyacetamide
N-(N',N'-diethylaminoethyl) phenyl-alpha-acetoxyacetamide
N-hydroxyethylthioethylphenyl-alpha-acetoxyacetamide
N-(2-phenylethanol) phenyl-alpha-acetoxyacetamide
N,N-dibenzyl phenyl-alpha-acetoxyacetamide
N-hydroxyethoxyethyl phenyl-alpha-acetoxyacetamide
N-diphenylmethyl phenyl-alpha-acetoxyacetamide
N-p-fluorobenzyl phenyl-alpha-acetoxyacetamide
N-p-methylbenzyl phenyl-alpha-acetoxyacetamide
N-p-chlorophenethyl phenyl-alpha-acetoxyacetamide
N-phenylpropyl phenyl-alpha-acetoxyacetamide
N-phenylbutyl phenyl-alpha-acetoxyacetamide.

6. The phenyl-alpha-acyloxyacetamide compound of claim 4 wherein the compound is a member selected from the group consisting of:

N-ethyl diphenyl-alpha-acetoxyacetamide
N-phenethyl diphenyl-alpha-acetoxyacetamide
N-ethyl diphenyl-alpha-phenylacetoxyacetamide
N-phenethyl diphenyl-alpha-phenylacetoxyacetamide
N-isopropyl diphenyl alpha-acetoxyacetamide
N-t-butyl diphenyl alpha-acetoxyacetamide
N-benzyl diphenyl-alpha-acetoxyacetamide
N-allyl diphenyl-alpha-acetoxyacetamide
N,N-diethyl diphenyl-alpha-acetoxyacetamide
N-(N',N'-diethylaminoethyl) diphenyl-alpha-acetoxyacetamide
N-P-chlorobenzyl diphenyl-alpha-acetoxy-acetamide
N-P-methoxybenzyl diphenyl-alpha-acetoxy-acetamide
N-P-methoxyphenethyl diphenyl-alpha-acetoxyacetamide
N-(N',N'-diethylaminopropyl) diphenyl-alpha-acetoxyacetamide
N-(N'',N'-dimethylamino propyl) diphenyl-alpha-acetoxyacetamide
N-p-fluorobenzyl diphenyl-alpha-acetoxyacetamide
N-p-methylbenzyl diphenyl-alpha-acetoxyacetamide
N-p-chlorophenethyl diphenyl-alpha-acetoxyacetamide
N-phenylpropyl diphenyl-alpha-acetoxyacetamide
N-phenylbutyl diphenyl-alpha-acetoxyacetamide.

7. Method of treatment to induce antipruritic, anti-inflammatory, antiarthritic, antieczematic, analgesic and tranquilizing effects in humans and animals comprising the administration of a composition comprising a therapeutic effective amount of a phenyl-alpha-acyloxyacetamide compound having the formula:

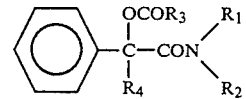

wherein $R_1$, $R_2$=H, alkyl or aralkyl group of saturated or unsaturated, straight or branched chain or cyclic form, having 1 to 25 carbon atoms, $R_3$=alkyl, aralkyl or aryl group of saturated or unsaturated, straight or branched chain or cyclic form, having 1 to 25 carbon atoms;

$R_4$=H, alkyl, aralkyl or aryl group of saturated or unsaturated, straight or branched chain or cyclic form, having 1 to 25 carbon atoms; and the hydrogen atom of the phenyl, $R_1$, $R_2$, $R_3$ or $R_4$ may be substituted by a nonfunctional halogen or a radical such as a lower alkyl or alkoxy having 1 to 9 carbon atoms; and the carbon atom of $R_1$ or $R_2$ may be substituted by a nonfunctional N, S or O, in a pharmaceutically acceptable vehicle for topical application to involved body areas or internal administration.

8. The phenyl-alpha-acyloxyacetamide of claim 7 wherein the compound is a member selected from the group consisting of:

N-ethyl phenyl-alpha-acetoxyacetamide
N-phenethyl phenyl-alpha-acetoxyacetamide
N-ethyl phenyl-alpha-phenylacetoxyacetamide
N-phenethyl phenyl-alpha-phenylacetoxyacetamide
N-ethyl phenyl-alpha-benzoyloxyacetamide
N-allyl phenyl-alpha-acetoxyacetamide
N-ethyl phenyl-alpha-lauroyloxyacetamide
N-phenethyl phenyl-alpha-linoleoyloxyacetamide
N-phenethyl phenyl-alpha-linolenoyloxyacetamide
N-isopropyl phenyl-alpha-acetoxyacetamide
N-t-butyl phenyl-alpha-acetoxyacetamide
N-p-chlorobenzyl phenyl-alpha-acetoxyacetamide
N-p-methoxybenzyl phenyl-alpha-acetoxyacetamide
N-p-methoxyphenethyl phenyl-alpha-acetoxyacetamide
N-(3,4-dimethoxyphenethyl) phenyl-alpha-acetoxyacetamide
N-(N',N'-diethylaminoethyl) phenyl-alpha-acetoxyacetamide
N-hydroxyethylthioethylphenyl-alpha-acetoxyacetamide
N-(2-phenylethanol) phenyl-alpha-acetoxyacetamide
N,N-dibenzyl phenyl-alpha-acetoxyacetamide N-hydroxyethoxyethyl phenyl-alpha-acetoxyacetamide
N-diphenylmethyl phenyl-alpha-acetoxyacetamide
N-p-fluorobenzyl phenyl-alpha-acetoxyacetamide
N-p-methylbenzyl phenyl-alpha-acetoxyacetamide
N-p-chlorophenethyl phenyl-alpha-acetoxyacetamide
N-phenylpropyl phenyl-alpha-acetoxyacetamide
N-phenylbutyl phenyl-alpha-acetoxyacetamide
N-benzyl phenyl-alpha-acetoxyacetamide.

9. The phenyl-alpha-acyloxyacetamide of claim 7 wherein the compound is a member selected from the group consisting of:
N-ethyl diphenyl-alpha-acetoxyacetamide
N-phenethyl diphenyl-alpha-acetoxyacetamide
N-ethyl diphenyl-alpha-phenylacetoxyacetamide
N-phenethyl diphenyl-alpha-phenylacetoxyacetamide
N-isopropyl diphenyl alpha-acetoxyacetamide
N-t-butyl diphenyl alpha-acetoxyacetamide
N-benzyl diphenyl-alpha-acetoxyacetamide
N-allyl diphenyl-alpha-acetoxyacetamide
N,N-diethyl diphenyl-alpha-acetoxyacetamide
N-(N',N'-diethylaminoethyl) diphenyl-alpha-acetoxyacetamide
N-P-chlorobenzyl diphenyl-alpha-acetoxy-acetamide
N-P-methoxybenzyl diphenyl-alpha-acetoxy-acetamide
N-P-methoxyphenethyl diphenyl-alpha-acetoxyacetamide
N-(N',N'-diethylaminopropyl) diphenyl-alpha-acetoxyacetamide
N-(N',N'-dimethylamino propyl) diphenyl-alpha acetoxyacetamide
N-p-fluorobenzyl diphenyl-alpha-acetoxyacetamide
N-p-methylbenzyl diphenyl-alpha-acetoxyacetamide
N-p-chlorophenethyl diphenyl-alpha-acetoxyacetamide
N-phenylpropyl diphenyl-alpha-acetoxyacetamide
N-phenylbutyl diphenyl-alpha-acetoxyacetamide.

10. The method of claim 7 wherein the compound is a member selected from the group consisting:
N-ethyl phenyl-alpha-acetoxyacetamide
N-phenethyl phenyl-alpha-acetoxyacetamide
N-ethyl phenyl-alpha-phenylacetoxyacetamide
N-benzyl phenyl-alpha-acetoxyacetamide
N-phenethyl phenyl-alpha-phenylacetoxyacetamide
N-ethyl phenyl-alpha-benzoyloxyacetamide
N-allyl phenyl-alpha-acetoxyacetamide
N-ethyl phenyl-alpha-lauroyloxyacetamide
N-phenethyl phenyl-alpha-linoleoyloxyacetamide
N-phenethyl phenyl-alpha-linolenoyloxyacetamide
N-isopropyl phenyl-alpha-acetoxyacetamide
N-t-butyl phenyl-alpha-acetoxyacetamide
N-p-chlorobenzyl phenyl-alpha-acetoxyacetamide
N-p-methoxybenzyl phenyl-alpha-acetoxyacetamide
N-p-methoxyphenethyl phenyl-alpha-acetoxyacetamide
N-(3,4-dimethoxyphenethyl) phenyl-alpha-acetoxyacetamide
N-(N',N'-diethylaminoethyl) phenyl-alpha-acetoxyacetamide
N-hydroxyethylthioethylphenyl-alpha-acetoxyacetamide
N-(2-phenylethanol) phenyl-alpha-acetoxyacetamide
N,N-dibenzyl phenyl-alpha-acetoxyacetamide
N-hydroxyethoxyethyl phenyl-alpha-acetoxyacetamide
N-diphenylmethyl phenyl-alpha-acetoxyacetamide
N-p-fluorobenzyl phenyl-alpha-acetoxyacetamide
N-p-methylbenzyl phenyl-alpha-acetoxyacetamide
N-p-chlorophenethyl phenyl-alpha-acetoxyacetamide
N-phenylpropyl phenyl-alpha-acetoxyacetamide; and
N-phenylbutyl phenyl-alpha-acetoxyacetamide.

11. The method of claim 7 wherein the compound is a member selected from the group consisting of:
N-ethyl diphenyl-alpha-acetoxyacetamide
N-phenethyl diphenyl-alpha-acetoxyacetamide
N-ethyl diphenyl-alpha-phenylacetoxyacetamide
N-phenethyl diphenyl-alpha-phenylacetoxyacetamide
N-isopropyl diphenyl alpha-acetoxyacetamide
N-t-butyl diphenyl alpha-acetoxyacetamide
N-benzyl diphenyl-alpha-acetoxyacetamide
N-allyl diphenyl-alpha-acetoxyacetamide
N,N-diethyl diphenyl-alpha-acetoxyacetamide
N-(N',N'-diethylaminoethyl) diphenyl-alpha-acetoxyacetamide
N-P-chlorobenzyl diphenyl-alpha-acetoxy-acetamide
N-P-methoxybenzyl diphenyl-alpha-acetoxy-acetamide
N-P-methoxyphenethyl diphenyl-alpha-acetoxyacetamide
N-(N',N'-diethylaminopropyl) diphenyl-alpha-acetoxyacetamide
N-(N',N'-dimethylamino propyl) diphenyl-alpha-acetoxyacetamide
N-p-fluorobenzyl diphenyl-alpha-acetoxyacetamide
N-p-methylbenzyl diphenyl-alpha-acetoxyacetamide
N-p-chlorophenethyl diphenyl-alpha-acetoxyacetamide
N-phenylpropyl diphenyl-alpha-acetoxyacetamide
N-phenylbutyl diphenyl-alpha-acetoxyacetamide.

12. Method of treatment to induce antripruritic, antiinflammatory, antiarthritic, antieczematic, analgesic and tranquilizing effects in humans and animals comprising the administration of a composition comprising, in combination, a therapeutic effect amount of a phenyl-alpha-acyloxyacetamide compound having the following formula:

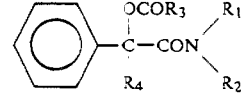

wherein
$R_1$, $R_2$=H, alkyl or aralkyl group of saturated or unsaturated, straight or branched chain or cyclic form, having 1 to 25 carbon atoms,
$R_3$=alkyl, aralkyl or aryl group of saturated or unsaturated, straight or branched chain or cyclic form, having 1 to 25 carbon atoms;
$R_4$=H, alkyl, aralkyl or aryl group of saturated or unsaturated, straight or branched chain or cyclic form, having 1 to 25 carbon atoms; and
the hydrogen atom of the phenyl, $R_1$, $R_2$, $R_3$ or $R_4$ may be substituted by a nonfunctional halogen or a radical such as a lower alkyl or alkoxy having 1 to 9 carbon atoms; and
the carbon atom of $R_1$ or $R_2$ may be substituted by a nonfunctional N, S or O; an effective amount a dermatologic agent effective as an antiyeast, antifungal, antibacterial, antiviral, anti-inflammatory, keratolytic, antipsoriatic, or antieczematic agent in a pharmaceutically acceptable vehicle for topical application to involved body areas or internal administration.

13. The composition of claim 12 wherein said agent is a member selected from the group consisting of clotrimazole, miconazole, nystatin, neomycin, gramicidin, haloprogin, griseofulvin, salicylic acid, sodium thiosulfate, selenium sulfide, zinc pyrithione, benzyl benzoate, crotamiton, lindane, phenol, methol, amphotericins, penicillins, corticosteroids, antihistamines, antibiotics, anthralin, or tar preparations.

14. The phenyl-alpha-acyloxyacetamide of claim 12 wherein the compound is a member selected from the group consisting of:
N-ethyl phenyl-alpha-acetoxyacetamide
N-phenethyl phenyl-alpha-acetoxyacetamide
N-ethyl phenyl-alpha-phenylacetoxyacetamide
N-phenethyl phenyl-alpha-phenylacetoxyacetamide
N-ethyl phenyl-alpha-benzoyloxyacetamide
N-allyl phenyl-alpha-acetoxyacetamide
N-ethyl phenyl-alpha-lauroyloxyacetamide
N-phenethyl phenyl-alpha-linoleoyloxyacetamide
N-phenethyl phenyl-alpha-linolenoyloxyacetamide
N-isopropyl phenyl-alpha-acetoxyacetamide
N-t-butyl phenyl-alpha-acetoxyacetamide
N-p-chlorobenzyl phenyl-alpha-acetoxyacetamide
N-p-methoxybenzyl phenyl-alpha-acetoxyacetamide
N-p-methoxyphenethyl phenyl-alpha-acetoxyacetamide
N-(3,4-dimethoxyphenethyl) phenyl-alpha-acetoxyacetamide
N-(N',N'-diethylaminoethyl) phenyl-alpha-acetoxyacetamide
N-hydroxyethylthioethylphenyl-alpha-acetoxyacetamide
N-(2-phenylethanol) phenyl-alpha-acetoxyacetamide
N,N-dibenzyl phenyl-alpha-acetoxyacetamide
N-hydroxyethoxyethyl phenyl-alpha-acetoxyacetamide
N-diphenylmethyl phenyl-alpha-acetoxyacetamide
N-p-fluorobenzyl phenyl-alpha-acetoxyacetamide
N-p-methylbenzyl phenyl-alpha-acetoxyacetamide
N-p-chlorophenethyl phenyl-alpha-acetoxyacetamide
N-phenylpropyl phenyl-alpha-acetoxyacetamide
N-phenylbutyl phenyl-alpha-acetoxyacetamide
N-benzyl phenyl-alpha-acetoxyacetamide.

15. The phenyl-alpha-acyloxyacetamide of claim 12 wherein the compound is a member selected from the group consisting of:
N-ethyl diphenyl-alpha-acetoxyacetamide
N-phenethyl diphenyl-alpha-acetoxyacetamide
N-ethyl diphenyl alpha-phenylacetoxyacetamide
N-phenethyl diphenyl-alpha-phenylacetoxyacetamide
N-isopropyl diphenyl alpha-acetoxyacetamide
N-t-butyl diphenyl alpha-acetoxyacetamide
N-benzyl diphenyl-alpha-acetoxyacetamide
N-allyl diphenyl-alpha-acetoxyacetamide
N,N-diethyl diphenyl-alpha-acetoxyacetamide
N-(N',N'-diethylaminoethyl) diphenyl-alpha-acetoxyacetamide
N-P-chlorobenzyl diphenyl-alpha-acetoxy-acetamide
N-P-methoxybenzyl diphenyl-alpha-acetoxy-acetamide
N-P-methoxyphenethyl diphenyl-alpha-acetoxyacetamide
N-(N',N'-diethylaminopropyl) diphenyl-alpha-acetoxyacetamide
N-(N',N'-dimethylamino propyl)diphenyl-alpha-acetoxyacetamide
N-p-fluorobenzyl diphenyl-alpha-acetoxyacetamide
N-p-methylbenzyl diphenyl-alpha-acetoxyacetamide
N-p-chlorophenethyl diphenyl-alpha-acetoxyacetamide
N-phenylpropyl diphenyl-alpha-acetoxyacetamide
N-phenylbutyl diphenyl-alpha-acetoxyacetamide.

16. The method of claim 12 wherein the compound is a member selected from the group consisting of:
N-ethyl phenyl-alpha-acetoxyacetamide
N-phenethyl phenyl-alpha-acetoxyacetamide
N-ethyl phenyl-alpha-phenylacetoxyacetamide
N-phenethyl phenyl-alpha-phenylacetoxyacetamide
N-ethyl phenyl-alpha-benzoyloxyacetamide
N-allyl phenyl-alpha-acetoxyacetamide
N-ethyl phenyl-alpha-lauroyloxyacetamide
N-phenethyl phenyl-alpha-linoleoyloxyacetamide
N-phenethyl phenyl-alpha-linolenoyloxyacetamide
N-isopropyl phenyl-alpha-acetoxyacetamide
N-t-butyl phenyl-alpha-acetoxyacetamide
N-p-chlorobenzyl phenyl-alpha-acetoxyacetamide
N-p-methoxybenzyl phenyl-alpha-acetoxyacetamide
N-p-methoxyphenethyl phenyl-alpha-acetoxyacetamide
N-(3,4-dimethoxyphenethyl) phenyl-alpha-acetoxyacetamide
N-(N',N'-diethylaminoethyl) phenyl-alpha-acetoxyacetamide
N-hydroxyethylthioethylphenyl-alpha-acetoxyacetamide
N-(2-phenylethanol) phenyl-alpha-acetoxyacetamide
N,N-dibenzyl phenyl-alpha-acetoxyacetamide
N-hydroxyethoxyethyl phenyl-alpha-acetoxyacetamide
N-diphenylmethyl phenyl-alpha-acetoxyacetamide
N-p-fluorobenzyl phenyl-alpha-acetoxyacetamide
N-p-methylbenzyl phenyl-alpha-acetoxyacetamide
N-p-chlorophenethyl phenyl-alpha-acetoxyacetamide
N-phenylpropyl phenyl-alpha-acetoxyacetamide
N-phenylbutyl phenyl-alpha-acetoxyacetamide
N-benzyl phenyl-alpha-acetoxyacetamide.

17. The method of claim 12 wherein the compound is a member selected from the group consisting of:
N-ethyl diphenyl-alpha-acetoxyacetamide
N-phenethyl diphenyl-alpha-acetoxyacetamide
N-ethyl diphenyl-alpha-phenylacetoxyacetamide
N-phenethyl diphenyl-alpha-phenylacetoxyacetamide
N-isopropyl diphenyl alpha-acetoxyacetamide
N-t-butyl diphenyl alpha-acetoxyacetamide
N-benzyl diphenyl-alpha-acetoxyacetamide
N-allyl diphenyl-alpha-acetoxyacetamide
N,N-diethyl diphenyl-alpha-acetoxyacetamide
N-(N',N'-diethylaminoethyl) diphenyl-alpha-acetoxyacetamide
N-P-chlorobenzyl diphenyl-alpha-acetoxy-acetamide
N-P-methoxybenzyl diphenyl-alpha-acetoxy-acetamide
N-P-methoxyphenethyl diphenyl-alpha-acetoxyacetamide
N-(N',N'-diethylaminopropyl) diphenyl-alpha-acetoxyacetamide
N-(N',N'-dimethylamino propyl) diphenyl-alpha-acetoxyacetamide
N-p-fluorobenzyl diphenyl-alpha-acetoxyacetamide
N-p-methylbenzyl diphenyl-alpha-acetoxyacetamide
N-p-chlorophenethyl diphenyl-alpha-acetoxyacetamide
N-phenylpropyl diphenyl-alpha-acetoxyacetamide
N-phenylbutyl diphenyl-alpha-acetoxyacetamide.

18. Method of treatment comprising administering an antipruritic or anti-inflammatory effect amount of a phenyl-alpha-hydroxyacetamide compound having the formula:

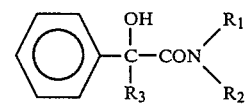

wherein
R$_1$, R$_2$=H, alkyl or aralkyl group of saturated or unsaturated, straight or branched chain or cyclic form, having 1 to 25 carbon atoms, R₃=H, aklyk, aralkyl or aryl group of saturated or unsaturated, straight or branched chain or cyclic form, having 1 to 25 carbon atoms, and the hydrogen atom of the phenyl, $R_1$, $R_2$ or $R_3$ may be substituted by a nonfunctional halogen or a radical such as a lower alkyl or alkoxy having 1 to 9 carbon atoms; and the carbon atom of R or $R_2$ may be substituted by a nonfunctional N, S or O; provided that both $R_1$ and $R_2$ are not N,N-diethyl, N,N-dipropyl, or N,N-dibutyl when $R_3$ =CH₃ and $R_4$=H, and $R_1$ is not ethyl or isopropyl when $R_2$ is H and $R_3$ is phenyl in a pharmaceutically acceptable vehicle for topical application to involved body areas or internal administration.

19. The phenyl-alpha-hydroxyacetamide of claim 18 wherein the compound is a member selected from the group consisting of:
N-ethyl phenyl-alpha-hydroxyacetamide
N-phenethyl phenyl-alpha-hydroxyacetamide
N-benzyl phenyl-alpha-hydroxyacetamide
N,N-diethyl phenyl-alpha-hydroxyacetamide
N-P-chlorobenzyl phenyl-alpha-hydroxyacetamide
N-P-fluorobenzyl phenyl-alpha-hydroxyacetamide
N-phenethyl diphenyl-alpha-hydroxyacetamide
N-benzyl diphenyl-alpha-hydroxyacetamide
N-P-chlorobenzyl diphenyl-alpha-hydroxyacetamide
N,N-diethyl diphenyl-alpha-hydroxyacetamide
N-(N',N'-diethylaminoethyl) diphenyl-alpha-hydroxyacetamide
N-p-fluorobenzyl diphenyl-alpha-hydroxyacetamide
N-isopropyl phenyl-alpha-hydroxyacetamide
N-t-butyl phenyl-alpha-hydroxyacetamide
N-(N',N'-diethylaminoethyl) phenyl-alpha-hydroxyacetamide
N-allyl phenyl-alpha-hydroxyacetamide
N-P-methoxybenzyl phenyl-alpha-hydroxyacetamide
N-P-methoxyphenethyl phenyl-alpha-hydroxyacetamide
N-(3,4-dimethoxyphenethyl) phenyl-alpha-hydroxyacetamide
N-hydroxyethylthioethyl phenyl-alpha-hydroxyacetamide
N-(N',N'-diethylaminopropyl) phenyl-alpha-hydroxyacetamide
N-(N',N'-dimethylaminopropyl) phenyl-alpha-hydroxy-acetamide
N-(N',N'-diethylaminopropyl) diphenyl-alpha-hydroxyacetamide
N-(N',N'-dimethylaminopropyl) diphenyl-alpha-hydroxyacetamide
N-P-methoxybenzyl diphenyl-alpha-hydroxyacetamide
N-P-methoxyphenethyl diphenyl-alpha-hydroxyacetamide
N-(3,4-dimethoxyphenethyl) diphenyl-alpha-hydroxyacetamide
N-hydroxyethylthioethyl diphenyl-alpha-hydroxyacetamide
N-t-butyl diphenyl-alpha-hydroxyacetamide
N-allyl diphenyl-alpha-hydroxyacetamide.

20. A phenyl-alpha-acyloxyacetamide compound selected from the group consisting of:
N-ethyl phenyl-alpha-acetoxyacetamide
N-phenethyl phenyl-alpha-acetoxyacetamide
N-ethyl phenyl-alpha-phenylacetoxyacetamide
N-phenethyl phenyl-alpha-phenylacetoxyacetamide
N-ethyl phenyl-alpha-benzoyloxyacetamide
N-allyl phenyl-alpha-acetoxyacetamide
N-ethyl phenyl-alpha-lauroyloxyacetamide
N-phenethyl phenyl-alpha-linoleoyloxyacetamide
N-phenethyl phenyl-alpha-linolenoyloxyacetamide
N-isopropyl phenyl-alpha-acetoxyacetamide
N-t-butyl phenyl-alpha-acetoxyacetamide
N-p-chlorobenzyl phenyl-alpha-acetoxyacetamide
N-p-methoxybenzyl phenyl-alpha-acetoxyacetamide
N-p-methoxyphenylethyl phenyl-alpha-acetoxyacetamide
N-(3,4-dimethoxyphenethyl) phenyl-alpha-acetoxyacetamide
N-(N',N'-diethylaminoethyl) phenyl-alpha-acetoxyacetamide
N-hydroxyethylthioethylphenyl-alpha-acetoxyacetamide
N-(2-phenylethanol) phenyl-alpha-acetoxyacetamide
N,N-dibenzyl phenyl-alpha-acetoxyacetamide
N-hydroxyethoxyethyl phenyl-alpha-acetoxyacetamide
N-diphenylmethyl phenyl-alpha-acetoxyacetamide
N-p-fluorobenzyl phenyl-alpha-acetoxyacetamide
N-p-methylbenzyl phenyl-alpha-acetoxyacetamide
N-p-chlorophenethyl phenyl-alpha-acetoxyacetamide
N-phenylpropyl phenyl-alpha-acetoxyacetamide
N-phenylbutyl phenyl-alpha-acyloxyacetamide; and
N-benzyl phenyl-alpha-acetoxyacetamide.

21. A diphenyl-alpha-acyloxyacetamide compound selected from the group consisting of:
N-ethyl diphenyl-alpha-acetoxyacetamide
N-phenethyl diphenyl-alpha-acetoxyacetamide
N-ethyl diphenyl-alpha-phenylacetoxyacetamide
N-phenethyl diphenyl-alpha-phenylacetoxyacetamide
N-isopropyl diphenyl alpha-acetoxyacetamide
N-t-butyl diphenyl alpha-acetoxyacetamide
N-benzyl diphenyl-alpha-acetoxyacetamide
N-allyl diphenyl-alpha-acetoxyacetamide
N,N-diethyl diphenyl-alpha-acetoxyacetamide;
N-(N',N'-diethylaminoethyl) diphenyl-alpha-acetoxyacetamide.

* * * * *